United States Patent [19]
Jones et al.

[11] Patent Number: 6,117,073
[45] Date of Patent: *Sep. 12, 2000

[54] INTEGRATED EMERGENCY MEDICAL TRANSPORTATION DATABASE SYSTEM

[76] Inventors: Scott J. Jones, 6926 Mimosa Dr., Carlsbad, Calif. 92009; Kevin C. Hutton, 4237 Corte de la Siena, San Diego, Calif. 92130

[*] Notice: This patent issued on a continued prosecution application filed under 37 CFR 1.53(d), and is subject to the twenty year patent term provisions of 35 U.S.C. 154(a)(2).

[21] Appl. No.: 09/033,440

[22] Filed: Mar. 2, 1998

[51] Int. Cl.[7] ................................................ A61B 5/00
[52] U.S. Cl. ................................ 600/300; 705/2; 705/3
[58] Field of Search .................................. 600/300, 301; 128/897, 898, 903, 904, 920; 705/2, 3

[56] References Cited

U.S. PATENT DOCUMENTS

| | | |
|---|---|---|
| 3,921,318 | 11/1975 | Calavetta . |
| 4,221,404 | 9/1980 | Shuffstall . |
| 4,236,332 | 12/1980 | Domo . |
| 5,146,439 | 9/1992 | Jachmann et al. . |
| 5,283,829 | 2/1994 | Anderson . |
| 5,327,341 | 7/1994 | Whalen et al. . |
| 5,465,206 | 11/1995 | Hilt et al. . |
| 5,483,443 | 1/1996 | Milstein et al. . |
| 5,508,912 | 4/1996 | Schneiderman . |
| 5,544,044 | 8/1996 | Leatherman . |
| 5,550,976 | 8/1996 | Henderson et al. . |
| 5,619,991 | 4/1997 | Sloane ..................................... 600/300 |

*Primary Examiner*—Eric F. Winakur
*Attorney, Agent, or Firm*—Knobbe, Martens, Olson & Bear, LLP

[57] ABSTRACT

An integrated medical database system for the emergency medical transportation business is disclosed. The system includes a dispatch module, clinical module, administration module and billing module. Each module may communicate data with one or more of the other modules to form a system incorporating data sharing, thus achieving an end-to-end automation of emergency medical care accounting. Internal consistency checks are performed by the system to ensure that proper treatments are performed according to a chosen diagnosis.

27 Claims, 17 Drawing Sheets

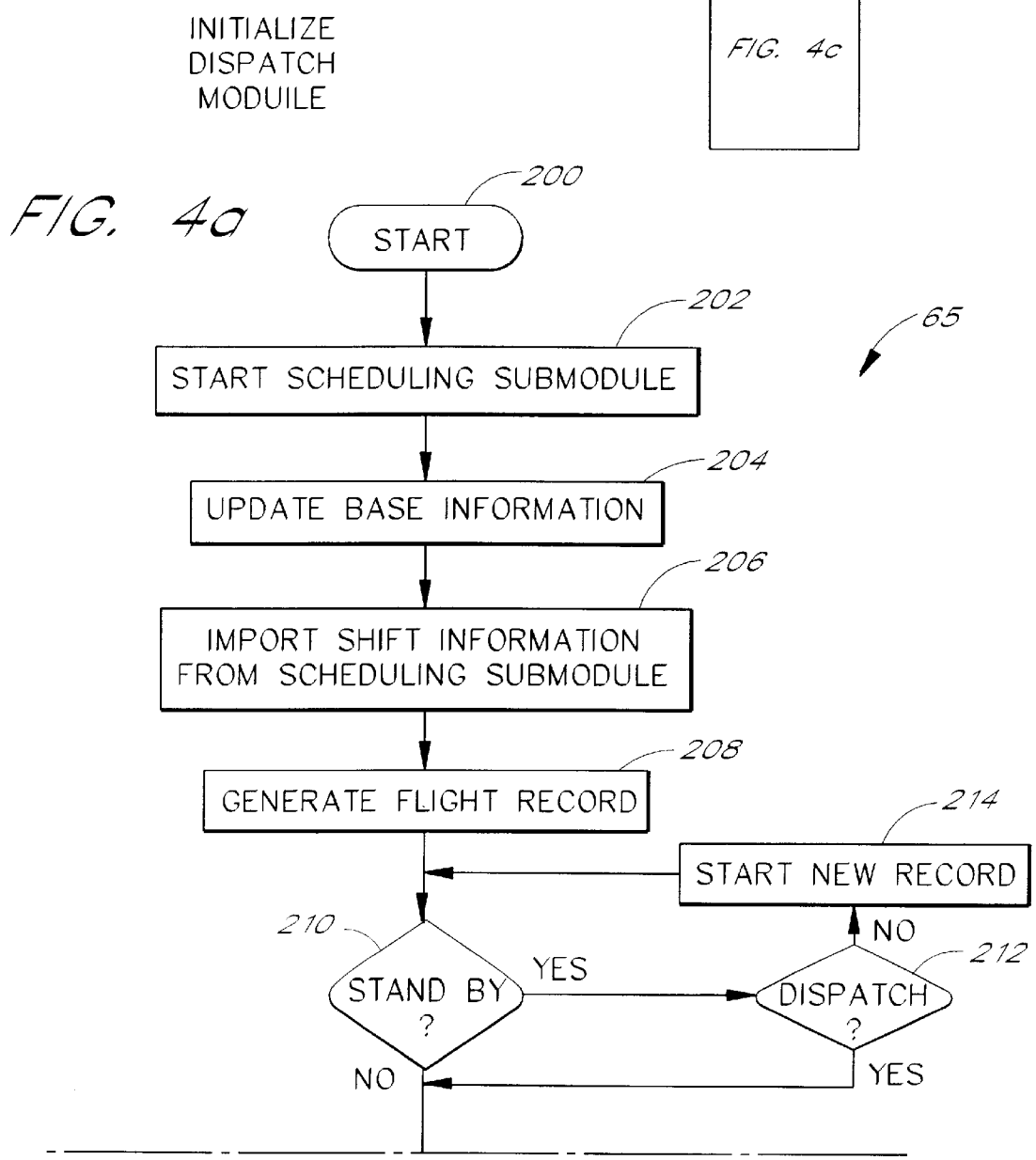

RUN PHYSICAL
EXAM PROCESS

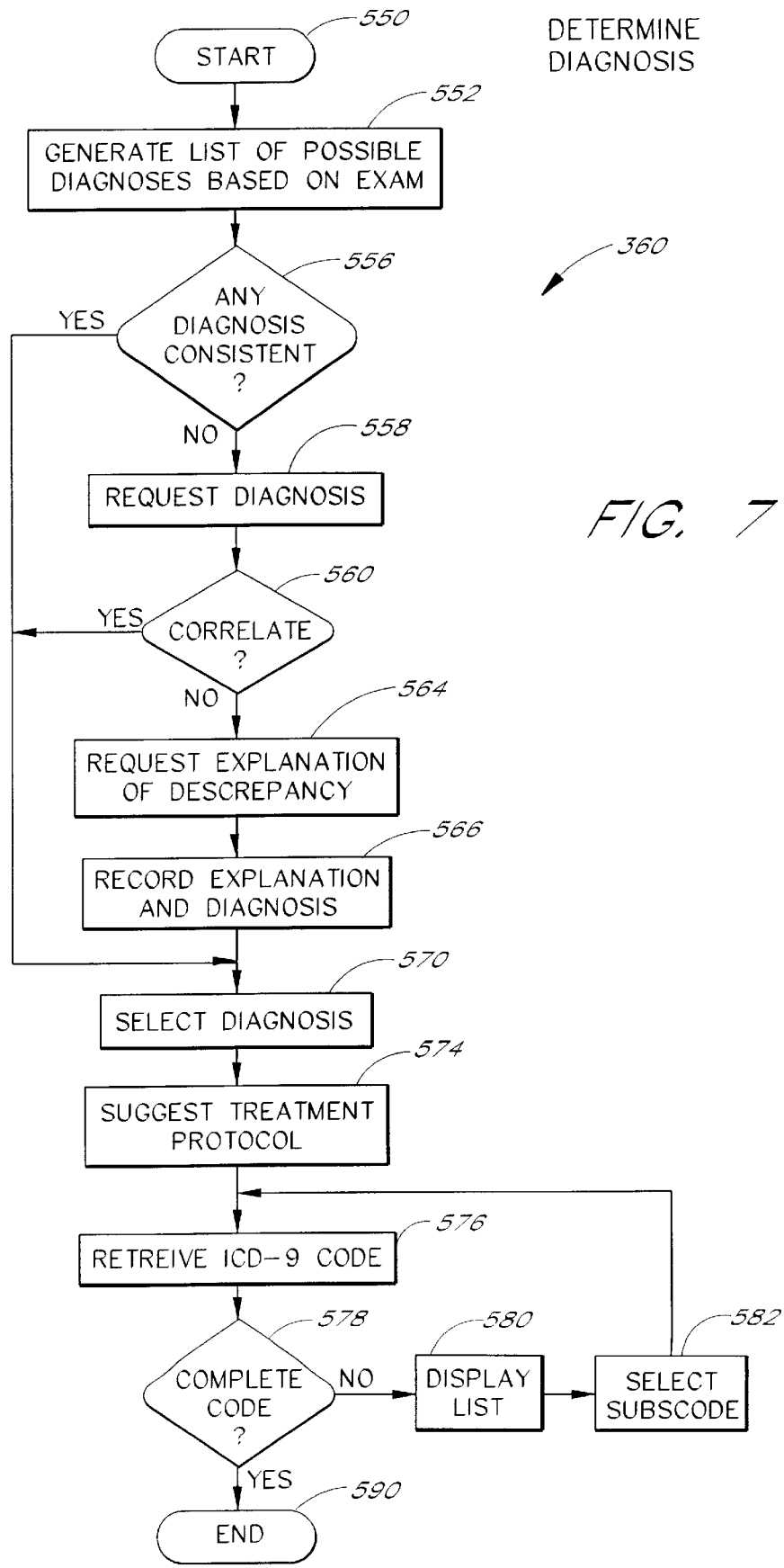

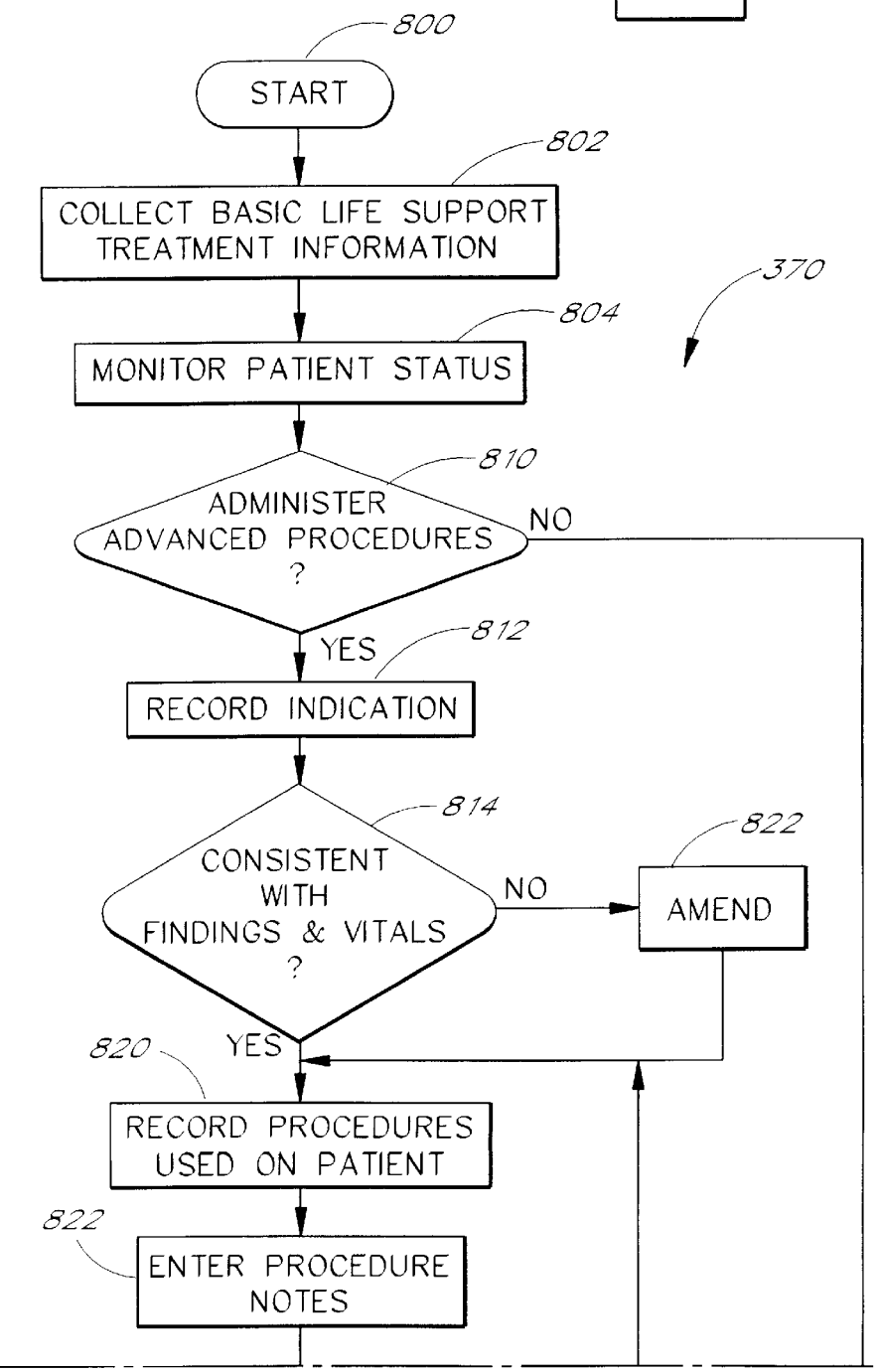

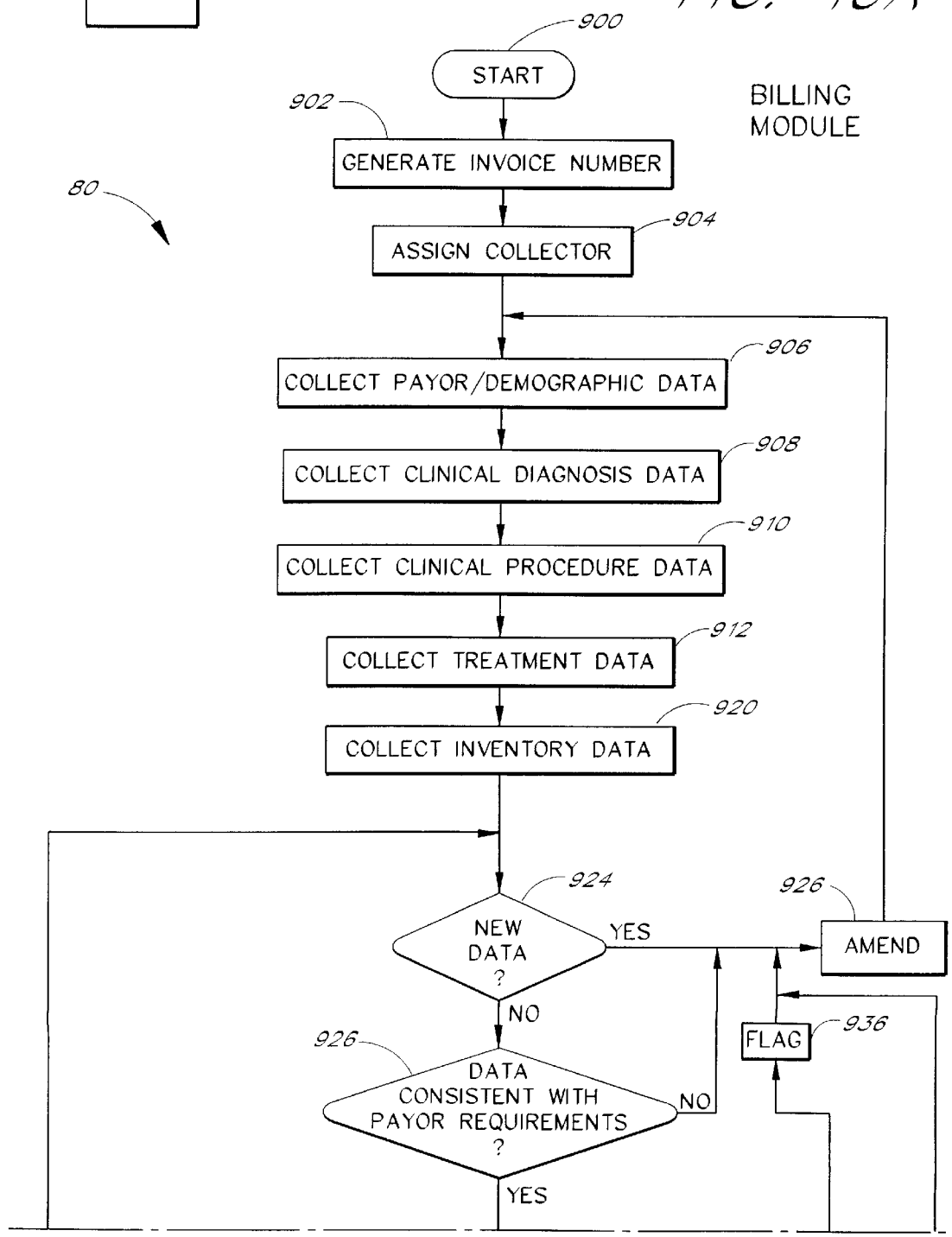

INTEGRATED EMERGENCY MEDICAL TRANSPORTATION DATABASE SYSTEM

BACKGROUND OF THE INVENTION

1. Field of the Invention

This invention relates to an integrated medical database system. More specifically, this invention relates to a medical database for the emergency medical transportation industry.

2. Description of the Related Technology

Current documentation procedures in the air medical transport industry are based on an inefficient paper and pencil technology. Important information is frequently collected on loose sheets of paper. In the environment of emergency medical transport, little time is available to neatly chart and document all pertinent and required information on a single document. Dispatch data, demographic data and clinical data are normally tracked as fragmented pieces of information which are later coalesced into a complete patient chart. In many cases, these data include the same information, thus forcing the input of redundant information. The resultant chart is therefore vulnerable to being incomplete and unreliable. In a medical setting, incomplete information can lead to disastrous clinical results.

This same technology is used to support industry quality improvement and billing procedures and submit letters of transport justification. This paperwork is usually carried out at a later date, prolonging account receivable times in many instances to the point of compromising and jeopardizing service compensation. Inventory stocking and tracking is similarly a victim of extended turnover times and is often incomplete and inaccurate.

The fragmentation throughout the medical transport environment is also evident in the myriad of entities throughout the country practicing different standards of care and documentation. As is the case in other segments of the healthcare industry, even seemingly simple tasks of communicating among the various entities, as well as among sections of a single providing entity, is severely hampered by the lack of a common communication format. This is especially evident when certain aspects of the system (such as computerized clinical laboratory result displays) have been upgraded with a uniquely tailored computerized system, while the remaining functions are still performed in an archaic manner. While the upgraded system may be effective for one singular aspect, such as dispatching, lab reporting, or chart dictating, the remainder of the system does not improve its effectiveness due to the other archaic components.

Although others have attempted to remedy this conflict, no fully integrated medical systems have been developed. For example, the Air Medical Software (Innovative Engineering of Lebanon, N.H.) provides computer software for dispatching emergency crews to accident scenes and managing flight information. However, it does not provide comprehensive integration of the flight information with a clinical diagnosis, billing system and administration system.

Air medical transport services suffer from a lack of understanding as to their effectiveness by governmental, academic and commercial organizations. A system is needed to collect solid statistics on how these systems can save lives and justify their existence and growth. Furthermore, medical crew evaluations and areas for improvement can be compared to known benchmarks after statistics on past service become widely available.

Therefore, what is needed is a comprehensive system that includes modules for dispatching emergency medical teams, tracking their movement to and from the accident scene, managing a clinical diagnosis and treatment and accurately billing the patient for the services rendered.

SUMMARY OF THE INVENTION

One embodiment of the present invention is a computerized integrated data management system for tracking a patient incident. The data management system includes: a first module capable of dispatching an emergency transport crew specific to a patient incident requiring emergency medical cary by the emergency transport crew; and a second module capable of receiving information from the first module and billing a patient appropriately for costs indicatve of the patient incident.

Another embodiment of the invention is a computerized integrated data management system for tracking a patient incident that includes: a first module capable of interpreting data relating to the medical condition of a patient involved in a patient incident requiring emergency medical care by an emergency medical transport crew and determining a diagnosis for the patient; and a second module capable of receiving information from the first module and billing the patient appropriately for the patient incident.

Yet another embodiment of the invention is a computerized method of generating a patient encounter record. The method includes the steps of: collecting flight information relating to an emergency transport crew dispatch; collecting patient information from a clinical encounter associated with a patient incident requiring emergency medical care by the emergency transport crew; and integrating the patient information with the flight information to produce an encounter record indicative of the patient's clinical encounter.

Still another embodiment of the invention is a method of diagnosing an illness in a patient. This method includes the computer implemented steps of: collecting information from a physical exam at the site of a patient's incident requiring emergency medical care by an emergency medical transport crew; determining a list of possible diagnoses based on the physical exam; and recording the diagnosis results in a centralized database of patient emergency medical information.

BRIEF DESCRIPTION OF THE DRAWINGS

FIG. 7 is a flow diagram illustrating the Determine Diagnosis and Rank process of FIG. 5.

DETAILED DESCRIPTION OF THE PREFERRED EMBODIMENT

Figure 1:
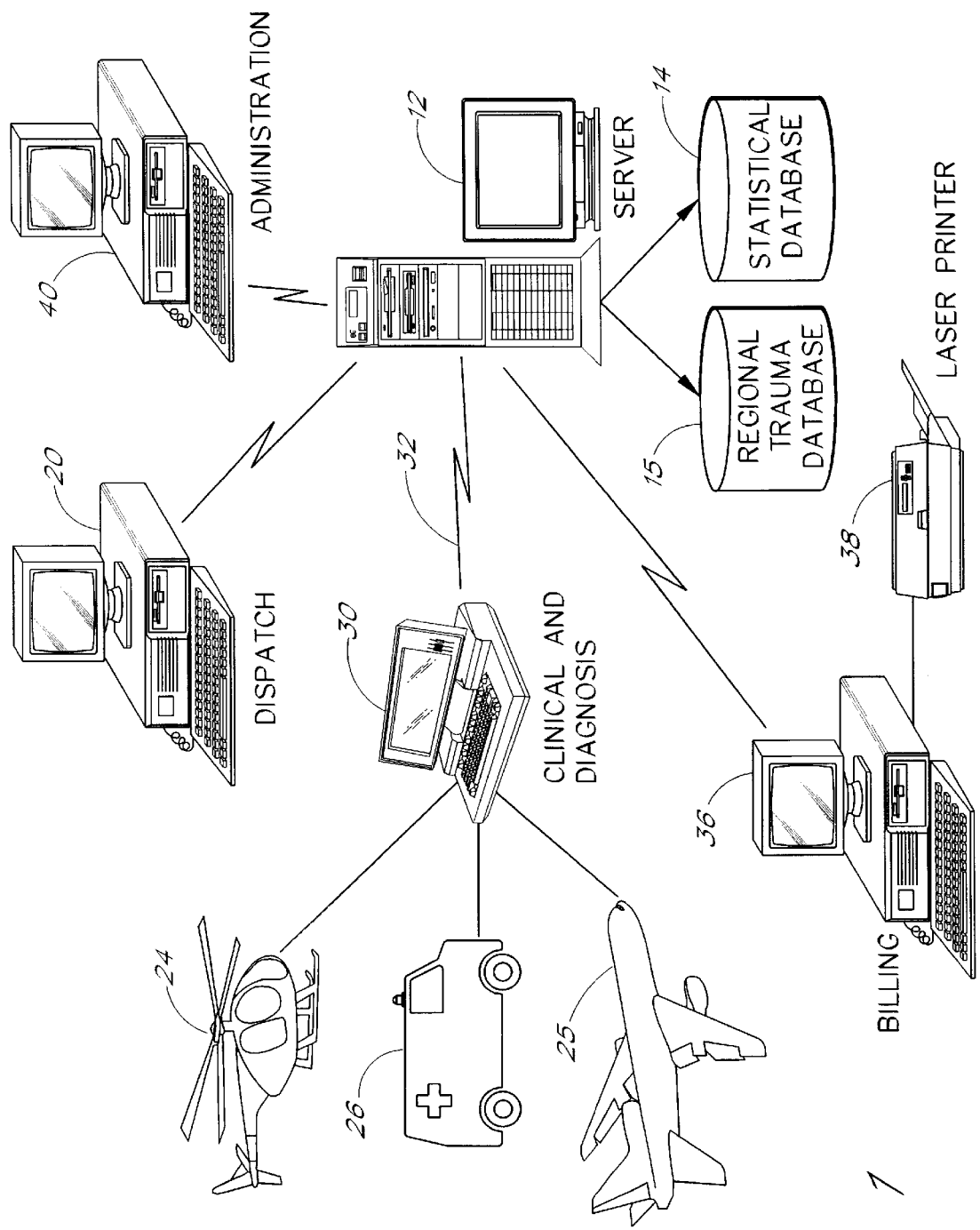
FIG. 1 is a diagram illustrating the on-line computing environment of the medical database system, including a dispatch interface computer, server computer, backup computer, clinical and diagnosis interface computer, administrative interface computer and billing interface computer.

The following detailed description presents a description of certain specific embodiments of the present invention. In this description, reference is made to the drawings wherein like parts are designated with like numerals throughout.

For convenience, the discussion of the invention is organized into the following principal sections: Introduction, Hardware Overview, Software Initialization, Data Flow Between Modules and Description of Software Modules.

Introduction

The present invention relates to an object oriented, interactive, international, client-server service for the medical transport industry. The service integrates all aspects of patient record documentation into a single complete electronic chart. A server computer provides chart database information access to multiple transport providers simultaneously by securely transmitting, storing and maintaining standardized patient data, for instance, using guidelines set forth by the Scrambling Standards Organization. Individual transport-providing entities, such as helicopter and ambulance companies, obtain coded access to this server via phone lines with a modem equipped personal computer. Security is maintained by assigning each entity a unique code or identifier. Integrated Services Digital Network (ISDN) lines, Digital Satellite Systems (DSS) or digital wireless systems may also be used for communication.

Each crew member involved in the patient's chart documentation, i.e. dispatcher, flight nurse, paramedic and physician, as well as administrator and collector, possess coded access to chart portions relevant to their responsibilities and level of care provided. The chart is then electronically generated from the compendium of the information entered in a standardized fashion and in accordance with minimum industry documentation requirements and the inventory of financial health care standards. The system provides complete and accurate chart documentation and maintains internal consistency between each separate module. Furthermore, any sentinel events are automatically referred to the appropriate, responsible party. A sentinel event is any action during the encounter that might require a further review. Examples of sentinel events are scene times exceeding 40 minutes, nonsensical data entry by an emergency transport crew member, supply shortages for equipment not utilized or repeated claim denials.

Billing can be submitted electronically to the appropriate party in an appropriate format which reduces the accounts receivable times for each patient encounter. Letters of justification are automatically generated as well as follow up letters and utilization review reports. Inventory reports and lists of necessary base supplies and medicines are also electronically updated to appropriate supply centers and administrators. Customized and research reports can also be provided rapidly.

Data security and an automatic backup are provided. Although the chart data is normally made the property of the respective transport service provider, the system can retain non-proprietary data to provide industry benchmarking, quality assurance analysis and clinical research opportunities. Such standardized data collection and documentation will furthermore enable the development of an Emergency Medical Services data library to assist in the justification and legislation of governmental preventive policies for public safety.

Hardware Overview

FIG. 1 provides an overview of the computer hardware involved in one embodiment of the medical database system. In this embodiment, the medical database system 10 includes a server computer 12. The server computer 12 can be based on any well-known microprocessor such as those manufactured by Intel, Motorola, IBM or DEC. The server computer should be able to enable rapid simultaneous access to many users of the system. In one preferred embodiment, the server computer 10 is an Intel Pentium class computer having at least 32 Megabytes of RAM and a four gigabyte hard disk drive and a 100 MHz processing speed. Of course, many other standard or non-standard computers may support an implementation of the present invention.

The database application may be programmed in, for instance, ACIUS's 4th Dimension language and used in conjunction with the 4D Server and Client program. Also, another alternative computer environment is Microsoft Corporation's Visual Basic language with the BackOffice 2.5 Client Server program. It can therefore run in a standard Windows/Macintosh point-and-click office environment, and requires no additional, specialized software programming from the user. Of course, other standard or non-standard computer environments may support an implementation of the present invention.

As illustrated, the server computer can access a statistical database 14 to store and extract statistical information from data entered during patient encounters. The collected statistics might include, for example, average scene and transport times, number of transport requests per demographic region and time of year, average number of advanced procedures performed by crew members and number of complications encountered. In addition, the database 14 can hold information relating to the average length of time to process claims by category and payment plan.

The server computer can also be linked to a regional trauma database 15. The database 15 holds information relating to local trauma centers, emergency medical practice and other local trauma-related information.

The dispatch module on the server computer 12 can be accessed via an interface to a dispatch computer 20, which might reside, for example, at the dispatch center that receives the initial call to deploy an emergency medical team. The dispatch computer 20 can provide just a communications interface to the server computer 12 so that it acts as computer terminal, or it can contain a portion of the dispatch module.

Based on the scene location and needs of the patient, the dispatch center might deploy a helicopter 24, airplane 25 or ambulance 26. The dispatch computer 20, as explained in more detail below, communicates with software for collecting information on the patient encounter and scheduling and deploying a crew to assist the injured patient. Within the medical database system 10, the helicopter 24, airplane 25 or ambulance 26 would include a portable computer 30 that is used by the emergency medical team during the patient encounter. A wireless connection 32 can be made by the portable computer 30 to the server computer 12 to update the database 14 after any data has been entered. The portable computer 30 can include clinical and diagnosis modules to assist the emergency medical team in treating the injured patient, or can act as a terminal to communicate with these modules on the server computer 12. As will be explained below, the clinical and diagnosis modules can help the emergency medical team determine the proper diagnosis and treatment of the patient.

The medical database system 10 also includes a billing computer 36 in communication with the server computer 12. The billing computer 36 interfaces with the server computer 12 to run the billing module for tracking inventory. The software billing module can be stored directly on the billing computer 36 or, alternatively, stored on the server 12 and accessed via the billing computer 36. The billing module is used to track inventory and medical equipment. In addition, it is used during the patient encounter for providing billing functions within the medical database system 10. The billing computer 36 communicates with a laser printer 38 to provide printed reports and bills to hospitals, patients and medical centers.

An administration computer 40 interfaces with the server computer 12 to provide run administrative reports. These reports might relate to the statistical information contained in the statistical database 14. In addition, the administration computer 40 might run reports that relate to payroll, inventory, flight training or many other administrative issues.

It should be noted that the dispatch interface computer 20, portable computer 30 and billing computer 36 can communicate with the server computer 12 through a variety of mechanisms. For example, a wireless LAN or cellular network may connect each computer with one another. In another embodiment, dedicated or dial-up phone lines can be used to communicate between the different computers.

Software Initialization

Figure 2:
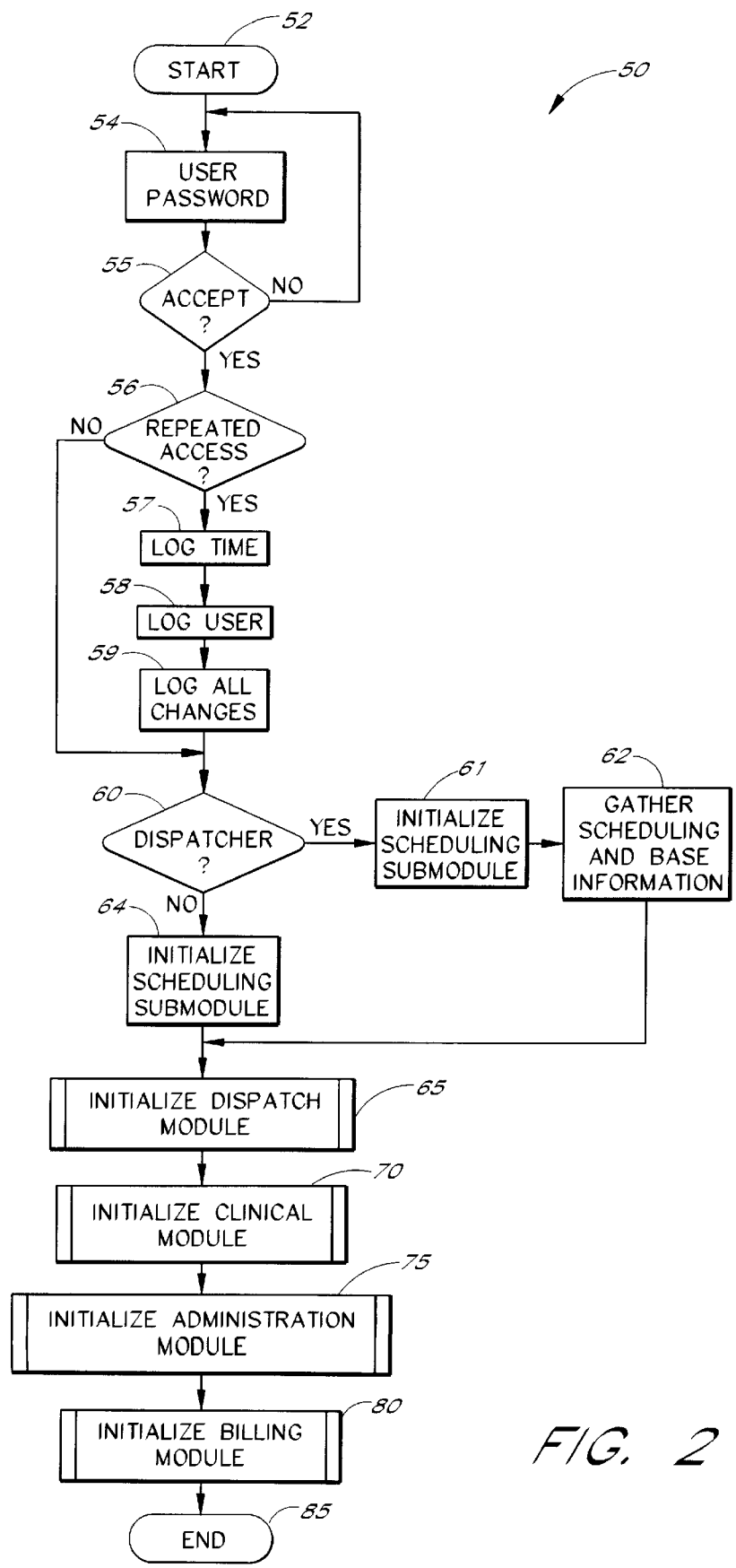
FIG. 2 is a flow diagram illustrating the overall process performed by the medical database system.

Referring now to FIG. 2, an overall process 50 of initializing the various software modules within the medical database system 10 is shown. Although FIG. 2 illustrates the initialization of all software modules in the system, it should be realized that each module can be initialized within a separate computer. For example, the dispatch module can be initialized within the dispatch computer 20 while the billing module is initialized within the billing system 36.

The process 50 begins at a start state 52 and then moves to state 54 wherein a user password is requested. If the user password is accepted at a decision state 55, the process 50 moves to a decision state 56 to determine whether this is a repeated access to the system. However, if the password is not accepted at the decision state 55, the process 50 returns to state 54 to re-request the user password.

If a determination is made at the decision state 56 that this is a repeated access, the process 50 moves to a state 57 to log the time of the access and then to a state 58 to log the identity of the user making the access. A log of the access changes to the system are then logged at a state 59. The process 50 then moves to a decision state 60 wherein a determination is made whether a dispatcher has initiated this call. However, if a determination is made at the decision state 56 that this was not a repeated access, the process 50 moves directly to the decision state 60.

If a determination is made at the decision state 60 that a dispatcher initiated this call, the process 50 moves to state 61 wherein a scheduling submodule is initialized. The scheduling submodule, as discussed above, tracks base information, crew schedules, helicopter flight times and the like. The process then moves to state 62 wherein the scheduling and base information from the dispatcher is shared and extracted into the clinical and diagnosis modules, and thereafter sent to the clinical and diagnosis computer interface 30 (FIG. 1). The process 50 then moves to a process state 65 wherein the dispatch module is initialized. However, if a determination was made at the decision state 60 that a dispatcher did not originate the call, the process 50 moves to state 63 and initializes the scheduling submodule. The process 50 then moves to process state 65 and initializes a dispatch module.

Figure 4B:
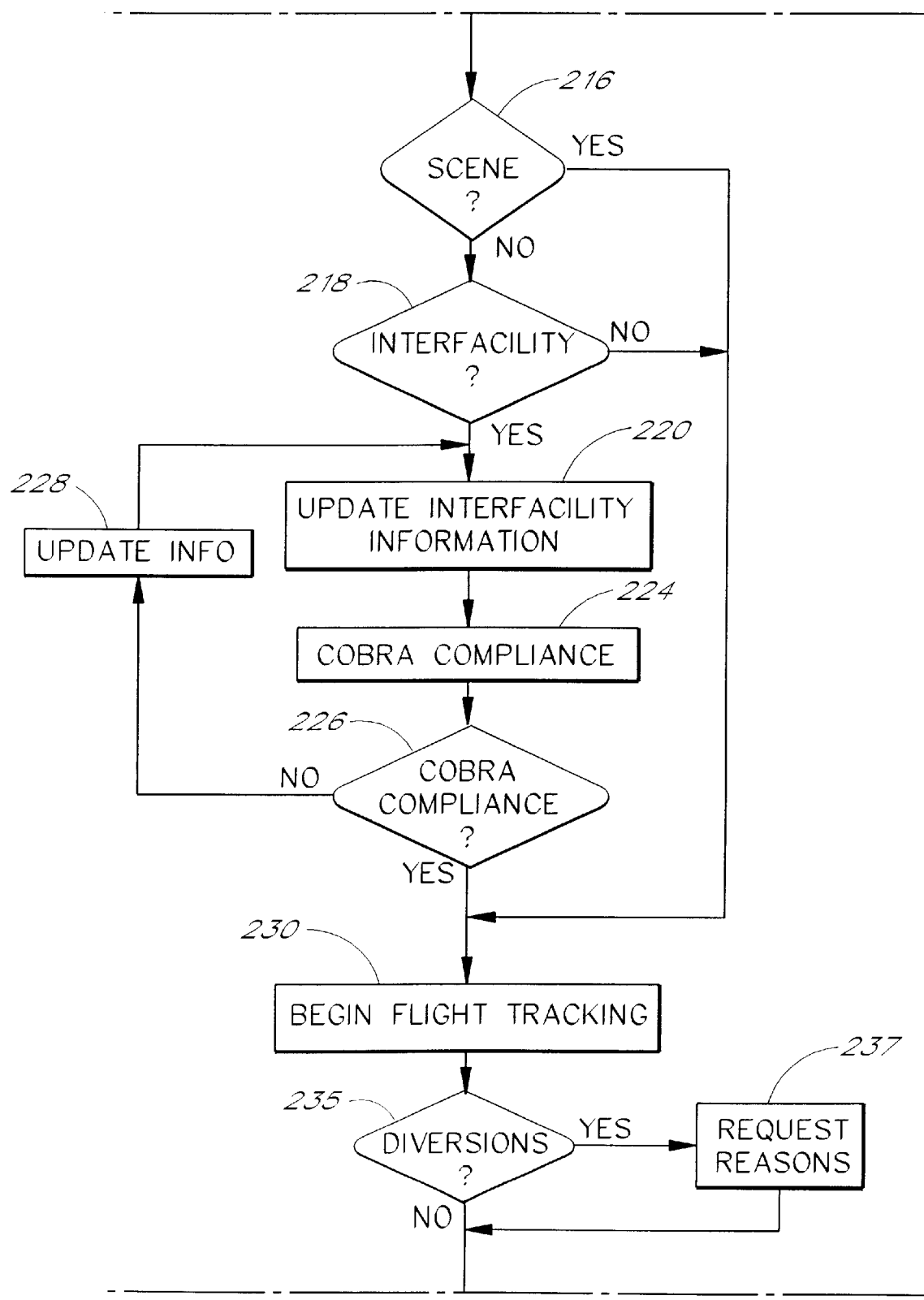
FIG. 4 is a flow diagram illustrating the Initialize Dispatch Module process of FIG. 2.
Figure 4C:
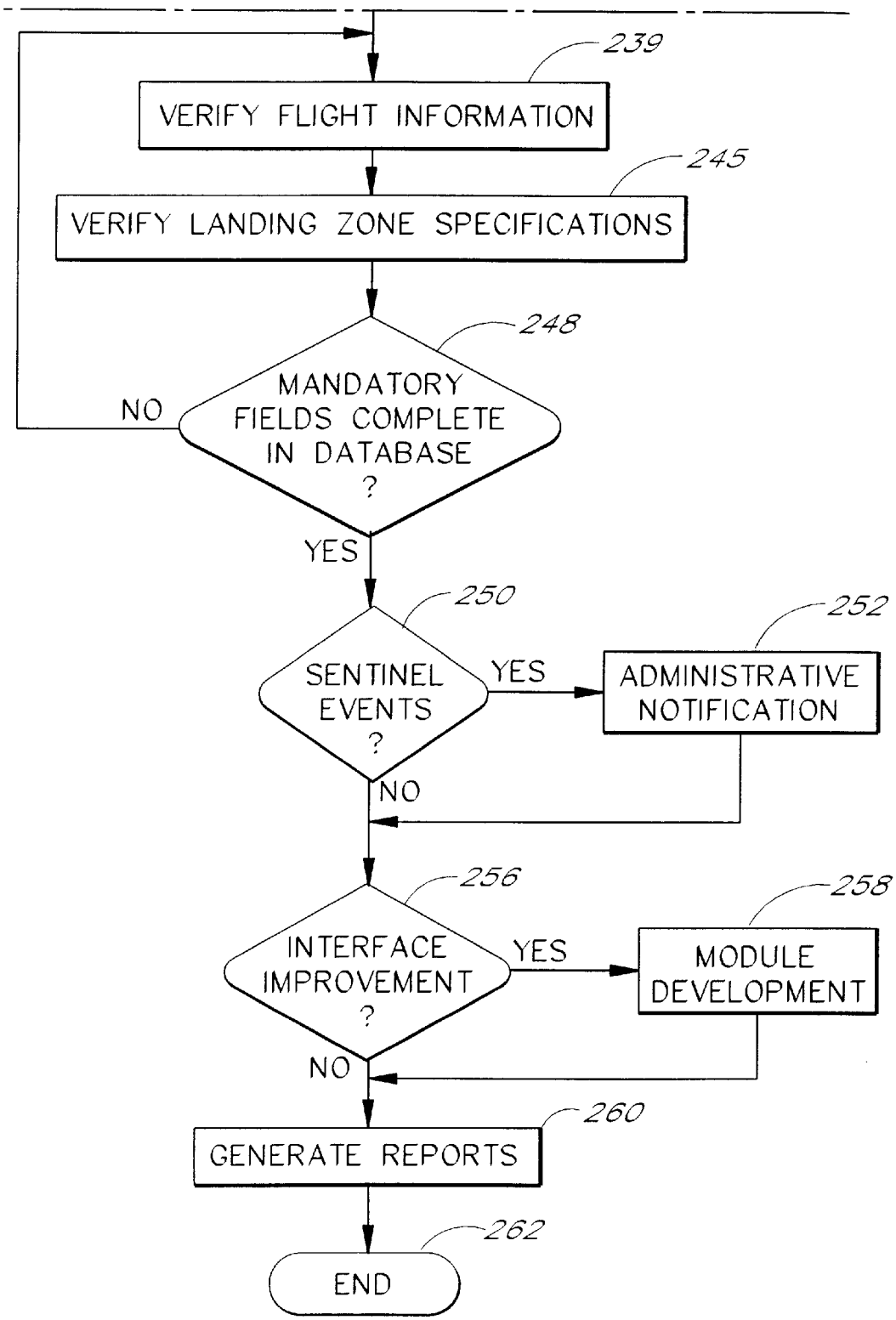

The dispatch module is divided into four interrelated submodules: Schedule, Standby, Flight and Transfer (not shown). The Scheduling submodule accomplishes the task of preparing schedules for the respective transport bases of an air medical service. The scheduling submodule is responsible for tracking dispatch, flight crew members, base physician, pilot (co-pilot), and stationed helicopters in service for a given shift. Data can be entered well in advance and updated up to the time a flight is actually dispatched. The process 65 of initializing and running a dispatch module is explained in more detail with reference to FIG. 4.

The Scheduling submodule shares shift information already entered in the Scheduling module to generate a flight record based on the date, time, and base from which the flight takes place. As mentioned above, upon flight dispatch, the dispatcher will receive the name of the current base physician, crew and helicopter information for verification.

The Standby submodule enables the dispatcher to collect information regarding the accident scene location, ground contacts, basic patient scenario and demographics prior to committing and dispatching a flight. This submodule allows agencies requesting air medical transport services to provide an early warning, verify the need for air transport and hence shorten the response and flight time to the accident scene.

The Transfer submodule coordinates patient transfers from one location to another. For example, a critical patient may need to be transported from a local hospital to a specialty hospital in order to receive a unique operation. The Transfer module manages the information associated with the patient transfer, such as origin, destination, purpose and the like.

The Flight submodule constitutes the main portion of the Dispatch module, and records information pertinent to the flight proper. Flights are tracked through timed and recorded position checks in accordance with Federal Aviation Agency (FAA) and Commission on Accreditation of Medical Transport requirements. Accident scenes are recorded with rendezvous and landing zone locations, address and zip codes as well as standard map coordinates, such as Thomas Brothers Reference points. In addition, waypoint/longitude-latitude location, the requesting agency, any ground contacts, and an appropriate communication frequency and the reason for call are all recorded by the flight submodule.

Further, the type and nature of call, base hospital, and name of the closest and receiving hospitals are collected. Mileage traveled and time stamping, including scene time, flight time and specialty times, such as crew change and pick up times as well as on site times, are calculated and recorded automatically from the information provided and dispatch feedback from flight crew. In addition, the reason and time for flight diversions and re-routings and elected ground transports with justification and alternate plans are entered into the system as well. Multiple flights can be orchestrated and recorded in parallel, while dispatcher and/or base physician change shifts during a flight—all data is constantly updated. When backup vehicles are required and dispatched, the flight information is transferred automatically from the primary responding crew to the backup crew.

Flight information is saved after verification as a dispatch record with a monthly flight number. A monthly American Air Medical Service (AAMS) record can then be automatically generated. Flight information can be canceled at any time, as well as deleted completely from the database with the appropriate option.

Once the dispatch module has been initialized at the process 65, a clinical module is initialized at a process 70. The Clinical module is also divided into several submodules: patient demographics, basic incident description, treatment rendered prior to air medical service arrival, general assessment including vital signs, intake and output as well as trauma scores, physical exam by systems, impression and diagnosis, treatment including medications and advanced procedures, en route events, quality assurance, justification of transport, and patient disposition. A specialized neonatal submodule can also be accessed if necessary.

Although any submodule can be accessed to begin a chart, the submodules are normally ordered in the traditional clinical format. Patient demographic information is first taken automatically from the dispatch data, if available. The patient information is first completed; including flight reference, date, base, scene, reason for transport, scene, landing and scene times, patient name, age, sex, weight and race, allergies, current medications, past medical history, place of exam, language barrier existence, type of call, nature of call, response such as night flight, in/out county intensive care unit to intensive care unit (icu—icu), transport team only, out county emergency department to emergency department (ed—ed) or emergency transport service with no charge.

Incident information, including the occurrence time, incident type (for example, motor vehicle accident, gun shot, fall, stabbing, drowning, loss of consciousness, pedestrian, cerebrovascular accident, chest pain, arrest, burn), type and description of accident (damage, extrication, loss of consciousness, other) can then be entered. Next, any treatment that was provided prior to air medical crew arrival is entered into the system. The name of first responders, along with the level of care provided and type of immobilization, airway management, intravenous access, cardiopulmonary resuscitation, medications and other treatments are recorded. The patient's Glasgow, CRAMS and Champion trauma scores are recorded separately, and in such a manner that consistency amongst them is assured.

The patient's vital signs, including systolic/diastolic blood pressure, pulse rate, respiratory rate, pulse oximetry, fluid intake/output along with the time of measurement are recorded. In addition, the arrival time of the aircraft on the scene, departure and hospital arrival times are once again displayed. Other important data pertinent to vital signs can be recorded in this module.

The physical examination portion is also divided into sections related to particular physiological components. A default standard normal examination for each system is provided, wherein all or portions thereof can be selected. Results can be typed, or selected from standard examination result options. The first examination is a neurological examination with input options such as alert, oriented times three, full recall, pupils equal and round and reactive to light and moving all extremities. The next examination is a skin exam with options such as good color, warm and dry, capillary refill less than 2 seconds, pulses well palpable. A head, eyes, ears, nose and throat exam can be performed, followed by a neck and chest examination. A cardiac examination having options such as regular rate and rhythm, no murmur rubs or gallop, and normal sinus rhythm on the monitor can be performed. The next examination can be abdominal, followed by pelvic and extremities examinations.

Once the results of these standard body examinations are received by the system, the physicians diagnoses are entered. In addition, the system generates pre-set diagnoses based on the results it has received during the clinical examination. Many of the results can be automatically recorded by having the monitoring equipment hooked directly into the portable computer system. Industry standard ICD-9 billing codes for each diagnosis can then be automatically determined and recorded by the system. These codes are used by the billing module to generate statements to the patient.

A treatment plan is next entered into the system by the emergency team. The treatment that occurred prior to the arrival of the air medical crew is automatically completed from the aforementioned section, if provided. Equipment used (Electrocardiogram, vital sign monitor, pulse oximeter, suction devices, ventilator, etc.), respiratory management, as well as intravenous access by crew, and neurological immobilization techniques (cervical collar, long/short back board, ked sled, etc.) and miscellaneous techniques (temperature measurements, bulb syringe, suction catheter, etc.) are recorded. All medications other than those applied under the standard advanced cardiac life support protocols are recorded from an extensive list within the system. Advanced procedures with procedure-specific documentation are recorded accurately. These include intubation, chest tube placement, pericardiocentesis, invasive line placement, advance cardiac life support, special medication administration, Mannitol infusion or Solumedrol administration.

Special documentation for the advanced procedure of intubation/cricothyrotomy includes the use (or mouse) of rapid sequence intubation techniques, route of successful intubation along with tube size, best visualization procedure, depth at which tube is secured, and confirmation technique of tube placement. Identification of successful and unsuccessful intubation medical crews can also tracked as a way to identify possible crew training issues. Pulse oximetry recordings can be performed before or after the procedure. Extensive choices are available to comment on the procedure and note any complications that were encountered by the medical team. The medications used during this procedure are recorded in a special medications submodule.

The special medications submodule records, in addition to rapid sequence intubation (RSI) medications, the name and dose of the medication given along with the identification of the administering crew member in accordance with Joint Commission on Accreditation of Health Care Organization Requirements (JCAHO). Any comments associated with the drug administration and ensuing complications can be recorded in this submodule.

Special documentation for any chest tube placement procedure is included in the system to record the patient's indication, type of technique (tube versus needle), identification of successful and unsuccessful performers, location of placement, size of tube and time of placement. In addition, the aspirate type and amount are recorded. Again, pulse oximetry measurements pre and post procedure are recorded into the system. Comments and complications ensuing from the procedure are as above recorded.

For pericardiocentesis, the procedure, time, identification of successful and unsuccessful performers, catheter and syringe sizes, aspirate amount and type, patient improvement as well as comments and complications (vascular damage, air embolus, etc.) are all included in the data acquisition by the system.

Invasive line procedure documentation includes identification of successful and unsuccessful performing crew, site of placement, type of access line, time of placement and comments and complications encountered. This can be used later for medical crew evaluations and training.

The advanced cardiac life support documentation includes the beginning and end of resuscitation times, medications in the order and dose administered, electricity administered (defibrillation, cardioversion), as well as other comments relating to the events that occurred. Vital signs and times are recorded or directly downloaded from the recording monitor.

The administration of particular drugs such as Mannitol are tightly controlled by law and require special documentation. The medical database system can complete this documentation by collecting the identification of the administering crew member, the patient's Glasgow Coma Score pre and post administration, dose given, indications and comments and complications encountered.

Similarly, Solumedrol administration also requires extra documentation, including identification of crew administering the medication, estimated level of neurological injury, dose and time given, as well as comments and complications encounters (allergic reaction, hypotension, etc.).

Other data is collected en route from the incident scene to the destination. The data collected can include the changed/unchanged patient status, name of person to whom report is given, name of accepting physician, and follow up status of transported patient. The process 70 of initializing and running a clinical module is explained in more detail with reference to FIG. 5.

The process 50 then moves to a process 75 and initializes an administration module for collecting and processing the information from the clinical encounter. The hierarchical structure of the system enables it to perform administrative services along with quality assurance as well. Indeed, from the chart's data, standard administrative reports can be automatically generated and sent to the appropriate personnel. Furthermore, a letter of justification for transport and interventions rendered is automatically generated in the required format from the chart components. With this same service, thank you letters and letters of follow up are directed as well to the responsible parties involved. The Emergency Medical Service can be provided with key preventive information on environmental health and public safety hazards encountered on scene by the transport crew. Also, internal reports and memos can be disseminated across the network of computers. And sentinel events such as those associated with neglect of care or failure to provide adequate care and safety, will immediately and automatically be called to the attention of the appropriate administrator to provoke corrective action. The administration module process 75 is explained in more detail with reference to FIG. 8.

Once the administration process has begun and the patient information is collected by the system 10, the process 50 moves to a process state 80 and initializes the billing module of the medical database system. The billing component takes advantage of the extensive patient information collected in the aforementioned modules. The demographic documentation is automatically incorporated from the dispatch and clinical modules. Precise billing for procedural interventions and inventory used in the treatment of a patient is exactly accounted for as was noted and recorded in the clinical component. In addition, procedures requiring the use of extensive inventory, such as intubations, chest tube placements, etc., are automatically evaluated for use of the required specific paraphernalia for completeness on the bill. When medications are administered, the billing component automatically selects the number of inventory unit amounts to be charged for from the total dose administered. The bill can then be processed electronically in the required format to the correct agency.

The same data used for billing is also used to update stock inventory on the respective transport vehicle and base after each encounter, to ensure adequate equipment supplies. Coupled to the supplier's inventory list, this information can automatically signal the need for delivery of equipment to the required base. Once the billing module is initialized at process 80, the overall process 50 terminates at an end state 85.

Data Flow Between Modules

Figure 3:
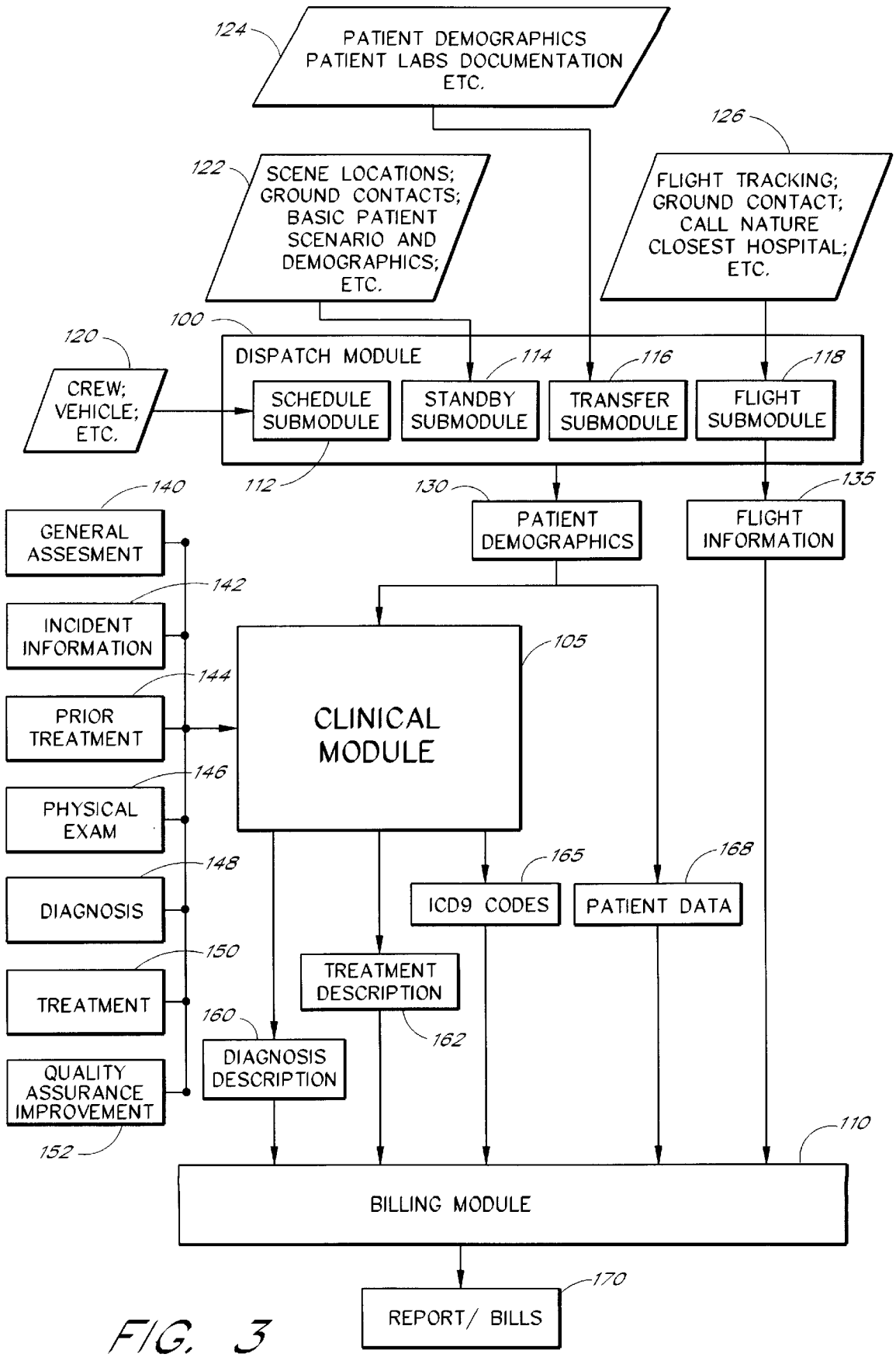
FIG. 3 is a block diagram illustrating the flow of data among the dispatch module, the clinical module, and the billing module, in one embodiment of the medical database system.

Referring now to FIG. 3, a block diagram of the data flow between the various modules within the medical database system is illustrated. FIG. 3 illustrates the flow of data between a dispatch module 100, clinical module 105 and billing module 110. The dispatch module 100 includes a scheduling submodule 112, a standby submodule 114, a transfer submodule 116 and a flight submodule 118. These various submodules process information received into the overall dispatch module 100. For example, crew information 120 is processed within the schedule submodule 112. In addition, scene information 122 is processed within the standby submodule 114.

Patient demographics and patient lab information 124 is processed within the transfer submodule 116. Flight tracking and other transportation information 126 is processed within the flight submodule 118. Once the various submodules within the dispatch module 10 have processed their respective information, a set of patient demographic information 130 and flight information 135 is made available to the remaining modules. For example, some of the patient demographic information 130 is imported into the clinical module 105.

In addition, many other pieces of data are placed within the clinical module 105. For example, the general assessment 140 of the patient that is taken by the emergency medical team is imported into the clinical module for further processing. In addition, other incident information 142 such as the type of incident (car accident, motorcycle accident, etc.) is sent to the clinical module 105. Prior treatment information 144 obtained from a physical exam of the patient or other information is also sent to the clinical module 105.

The prior treatment information might be important in determining whether the patient had already been treated for similar injuries thereby affecting the clinical diagnosis. Information collected from the physical exam 146 at the scene is also sent to the clinical module 105. In addition, any diagnosis 148 from the attending emergency medical team can be sent to the clinical module 105. It should be noted, as discussed below, that the medical database system 10 may also provide a diagnosis based on the physical exam information 146 and other information within the clinical module 105. This will be explained in more detail below.

Information relating to the treatment 150 of the patient is also sent to the clinical module 105. The medical database system 10 also includes a quality assurance database 152 which allows the emergency medical team to make suggestions or other comments that may be useful in additional treatments or incidents. For example, if the emergency medical team notes that a particular series of exam results has led to a unique diagnosis, this information can be input into the clinical module 105. Thus, the next time these same physical exam results are seen in a patient, the new diagnosis can be suggested to the emergency medical team.

Once the clinical module 105 has received its necessary information, data is output to the billing module 110. For example, a description of the diagnosis 160, a treatment description 162 or ICD-9 codes 165 can be sent from the clinical module 105 to the billing module 110. As is well known, ICD-9 codes are a set of unique codes referring to most well known medical procedures. These codes are used throughout the insurance industry to obtain payment for various medical procedures. In addition to the data from the clinical module 105, patient data 168 can be obtained from the patient demographic information 130. The flight information 135 can also be retrieved into the billing module 110. This information is then used within the billing module 110 to generate reports and bills 170. As can be expected, these reports and bills are sent to the various insurance companies and insurance providers. Thus, the medical database system 10 is an integrated system for providing many services within the medical industry.

Description of Software Modules
1) The Dispatch Module

Referring now to FIG. 4, a flow diagram illustrating the initialized dispatch module process 65 (FIG. 2) is described. The process 65 begins at a start state 200 and then moves to state 202 wherein the scheduling submodule is initialized. The scheduling submodule receives information 120 related to the emergency medical team crew, type of vehicle and other scheduling related information. The process 65 then moves to state 204 wherein any information relating to the transportation base is updated. The base includes the permanent physical location of the ambulance 26 or helicopter 24. Base information may also include the particular helicopter or ambulance chosen and the emergency medical team that will be in charge of the particular patient encounter, as well as base status (available, closed or reserved), and base-specific weather (visibility, precipitation, temperature, chill factor and cloud ceiling).

The process 65 then moves to state 206 wherein any shift information from the crew is imported into the scheduling submodule. A flight record is then begun at a state 208 and the process 65 moves to a decision state 210 to determine whether the crew is in a standby mode (e.g. waiting for a call). If a determination is made at the decision state 210 that the crew has been placed in a standby mode, the process 65 moves to a decision state 212 to determine whether a dispatch order has been given. If a dispatch order is not given, then a new record can be initiated by the dispatcher at a state 214 and the process returns to the decision state 210.

If a determination is made that the crew has received a call and is no longer in a standby mode at the decision state 210, or has been dispatched at the decision state 212, the process 65 moves to a decision state 216 (FIG. 4b) to determine whether the ambulance or helicopter will be transporting a patient from an incident scene to a hospital facility. If the type of transport is not from a scene to a hospital facility, the process 65 moves to a decision state 218 to determine whether an interfacility transfer, such as between hospitals, is required. If an interfacility transfer is required, the process 65 moves to state 220 and updates any interfacility information in the medical database system.

The process 65 then moves to state 224 to determine whether the interfacility transfer is in compliance with the Consolidated Budget Reconciliation Act (COBRA) or the Omnibus Budget Reconciliation Act (OBRA). The process 65 then moves to a decision state 226 to determine whether the interfacility transfer is within the COBRA compliance guidelines. If the interfacility transfer is not within COBRA compliance guidelines, then the process requests updated information at a state 228 and returns to state 220 to update the interfacility information.

If a determination is made at the decision state 226 that the interfacility transfer is within COBRA compliance, the process 65 moves to state 230 and begins to track the flight coordinates. In addition, if a determination was made at the decision state 216 that the type of transfer was from an accident scene, then the process 65 jumps to state 230 and begins flight tracking. Similarly, if a determination was made at the decision state 218 that the transfer was not an interfacility transfer, the process 65 jumps to state 230 and begins flight tracking. Some flights, such as for promotions, are neither from a scene or for an interfacility transfer.

Once flight tracking has begun at the state 230, the process 65 moves to a decision state 235 to determine whether any in-flight diversions have taken place. An in-flight diversion may arise because for example, a more acute emergency develops while the crew is en route. If a diversion has taken place, the reasons for the diversions are requested at a state 237. However, if no diversions take place during the flight, the process 65 verifies the flight information at a state 239 (FIG. 4c) and moves to a state 245 to verify the landing zone specifications for the helicopter. For instance, the specifications may relate to noise regulations, local high voltage lines or the like. The process 65 then moves to a decision state 248 to determine whether the mandatory fields in the database have been completed. The mandatory fields are data points that must be collected before a file can be closed. For example, the patient's name, address, and phone number might be chosen by the crew as mandatory fields. The file cannot be closed until these flagged fields contain data. If the mandatory fields in the database are not completed, the process 65 returns to state 239 to verify the flight information.

If the mandatory fields are completed in the system, the process moves to a decision state 250 to determine whether any sentinel events have occurred. A sentinel event is a major happening at the accident site which might require notification to the hospital. For example, an sentinel event might be arrival at an incorrect landing zone, arrival without a crew member, an incorrect patient description, defective equipment or a lack of the required medications. If a sentinel event has occurred at the decision state 250, the process 65 moves to a state 252 and prepares an administrative notification to the party that is to be notified of the sentinel event. The process 65 then moves to a decision state 256 wherein an inquiry is made to the emergency medical team whether any interface improvements, such as additional data fields, reordering data entry screens or field clarifications could be made into the software. Similarly, if no sentinel events occurred at the decision state 250, the process 65 moves to the decision state 256 to inquire about interface improvements. This request is a chance for the emergency medical team to request improvements for the medical database system.

If an interface improvement is made at the decision state 256, then a development module is opened at a state 258 and information is requested about what type of interface improvements could be made into the medical database system. The process 65 then moves to a state 260 to generate reports including flight records and transfer records. The process 65 then terminates at an end state 262.

2) The Clinical Module

Figure 5:
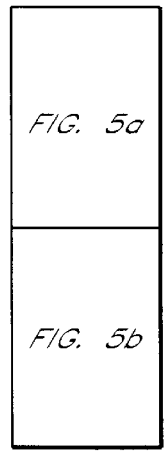
FIG. 5 is a flow diagram illustrating the Initialize Clinical Module process of FIG. 2.
Figure 5A:
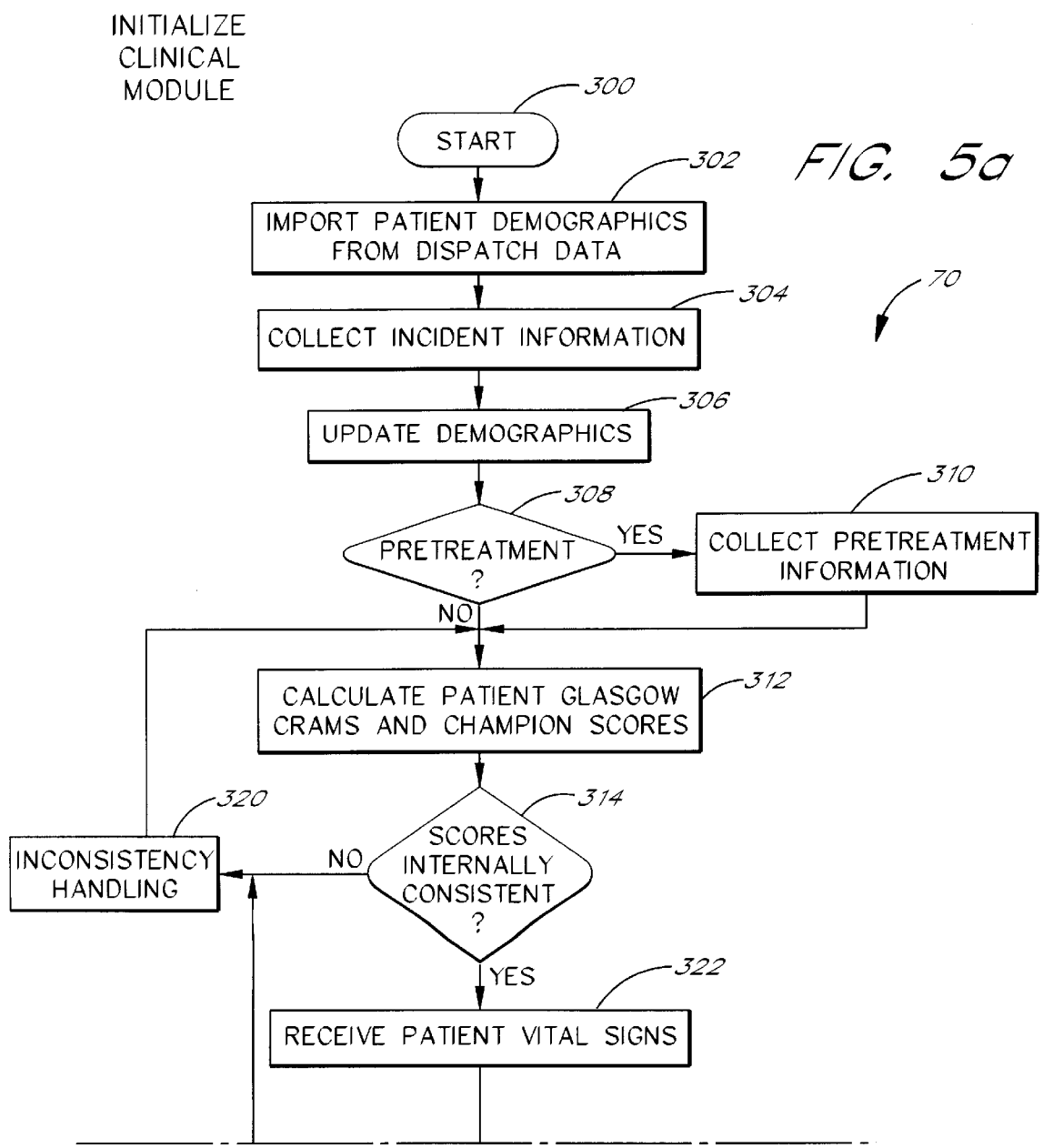

Referring to FIG. 5, the initialize clinical module process 70 of FIG. 2 is more specifically described. The process 70 begins at a start state 300 and moves to state 302 wherein the patient demographic information from the dispatch module is imported. The process 70 then moves to a state 304 wherein any information related to the incident is collected. The incident information may be, for example, the type of accident, location of accident, number of injured parties, etc. The process 70 then moves to a state 306 wherein the patient demographics are updated with the new information.

A determination is then made at a decision state 308 whether any pretreatment of the injured parties took place prior to arrival of the emergency medical team. If pretreatment did occur, the pretreatment information is collected at a state 310 and input into the system 10. However, if no pretreatment occurred, the process 70 moves to state 312 wherein the patient Glasgow, CRAMS, and Champion trauma scores are determined. Once these patient scores have been calculated, the process 70 moves to a decision state 314 wherein a determination is made whether the scores are internally consistent with one another. This internal consistency check is an important feature of the system because it offers a way to use the collected data to prevent incorrect treatments. If the data items are not internally consistent an error handling routine is begun at a state 320 and the process returns to the state 312. If the scores are internally consistent, the patient's vital signs are received at a state 322.

Figure 5B:
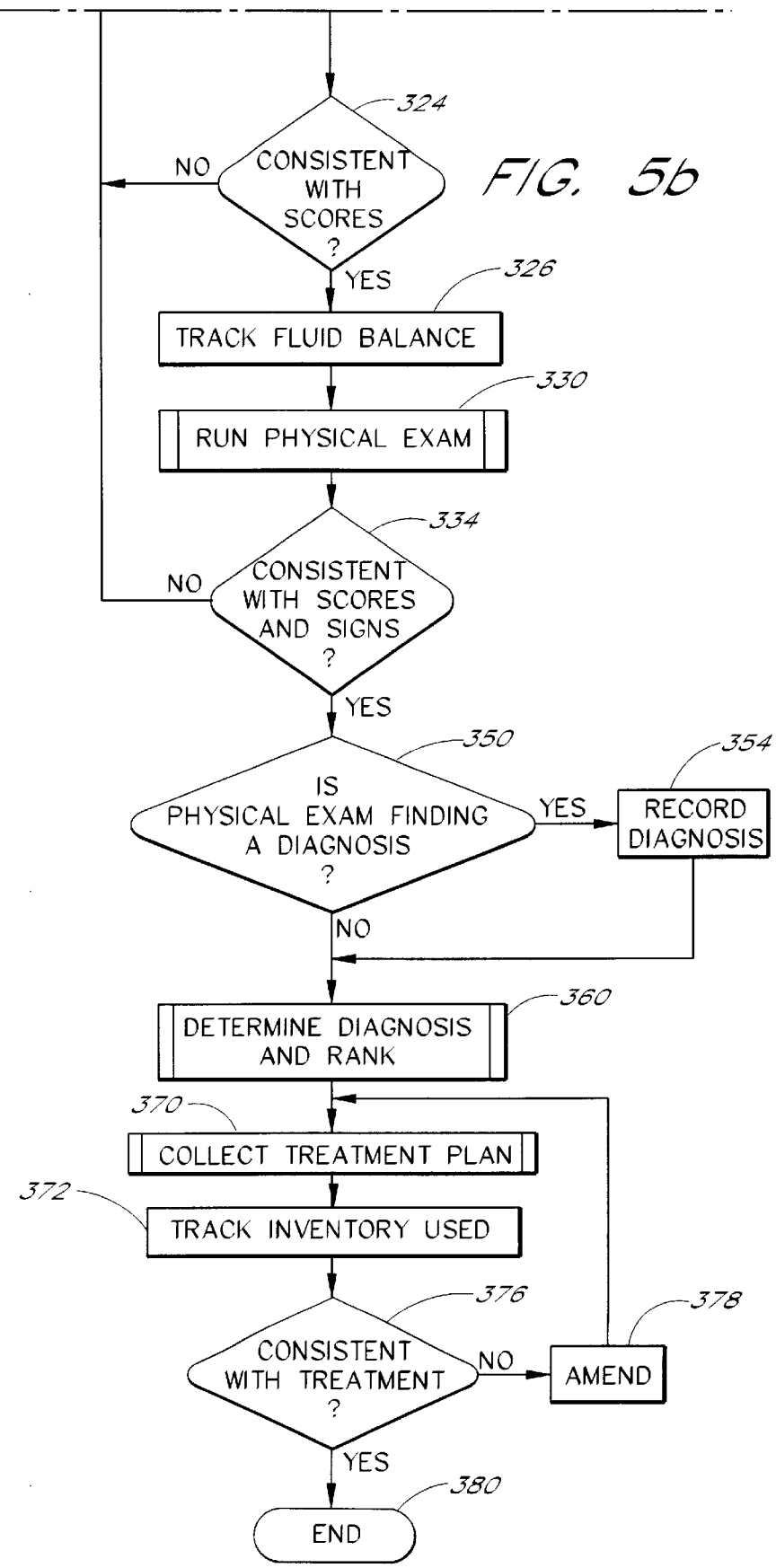

The process 70 then moves to a decision state 324 (FIG. 5*b*) to determine whether the patient's vital signs are consistent with the scores calculated at state 312. If the scores are not consistent, the process 70 returns to the inconsistency handling routine 320. This might be the case if the patient was not scored correctly or if the vital signs were input incorrectly into the system 10. If the scores are consistent, the process 70 moves to a state 326 wherein the fluid balance, including intravenous fluid administration, blood loss, and urine output of the patient is tracked.

A physical exam process 330 is then run on the patient, and will be explained in more detail below in reference to FIG. 6. Once the physical exam has been run at the process 330, a determination is made at a decision state 334 whether the results of the physical exam are consistent with the scores from the state 312 and vital signs from state 322. If a determination is made that the results of the physical exam are not consistent, the process 70 returns to the inconsistency handling routine 320. If a determination is made that the results of the physical exam at the process 330 are consistent with the scores and signs from states 312 and 322, the process 70 moves from decision state 334 to a decision state 350 to determine whether the physical exam finding is a diagnosis. Types of findings that are a diagnosis might be, for example, abrasions, lacerations, open fractures, dislocations, fractures with deformity, loss of consciousness and shock.

If a determination is made that the physical exam finding is a diagnosis, then the process 70 moves to a state 354 wherein the diagnosis is recorded into the medical database system. The process 70 then moves to a process 360 wherein the medical database system determines a diagnosis and rank for the patient. The diagnoses are ranked in accordance with the severity of the injury and level of compensation. The process 360 will be explained in more detail in reference to FIG. 7 below. Once the diagnosis and rank have been determined at the process 360 a process 370 is begun to collect the treatment information for the patient.

Once the treatment plan information is collected at the process 370 the inventory used during the treatment is tracked at a state 372. The process 70 then moves to a decision state 376 to determine whether the inventory used at the state 372 is consistent with the treatment determined at the process 370. If the treatment is inconsistent with the inventory used, the process 70 moves to a state 378 and allows an amendment to correct the procedure documentation so that the inventory will be correctly reflected the next time the procedure is logged into the medical database system. The process 70 then returns to process 370 to collect the treatment plan again. If a determination is made at the decision state 376 that the inventory used was consistent with the treatment, the process 70 terminates at an end state 380.

A) The Physical Exam Process

Figures 6, 6A:
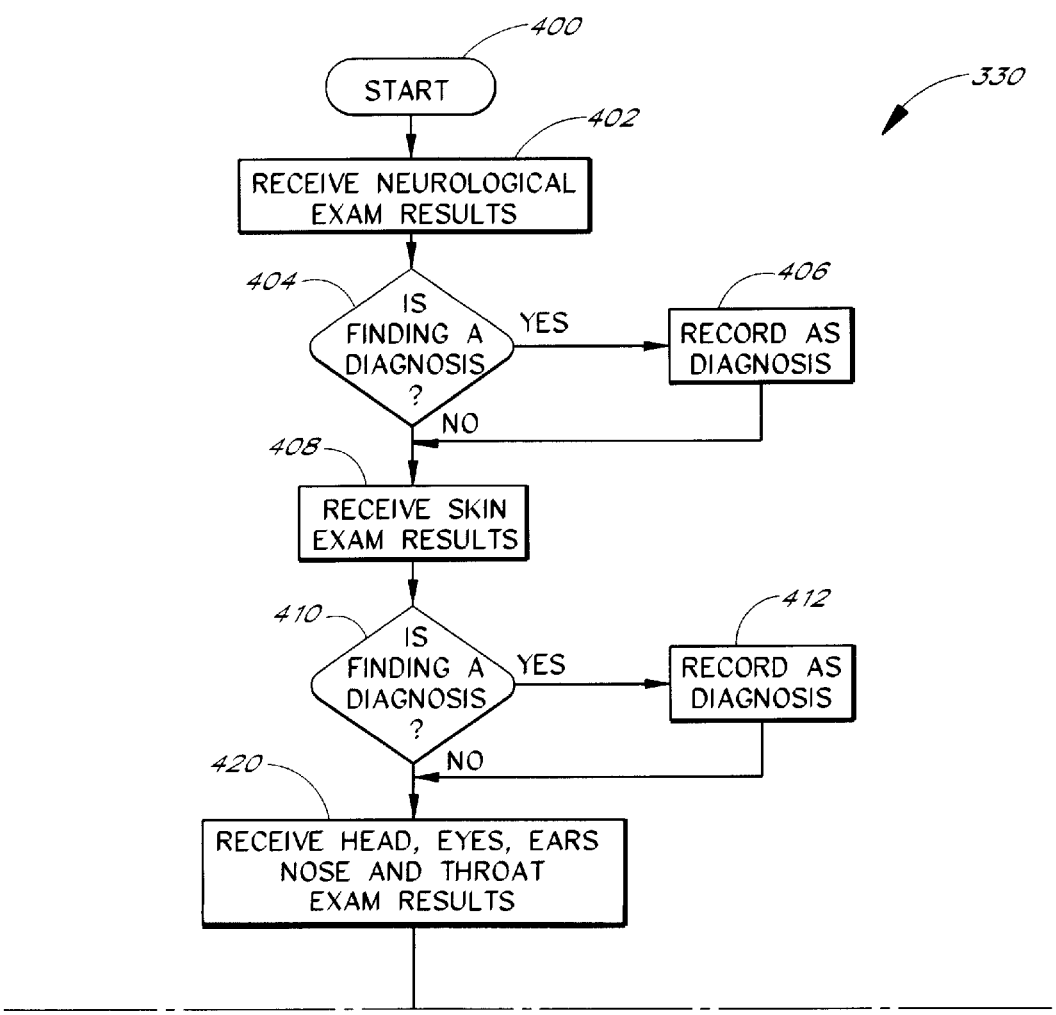
FIG. 6 is a flow diagram illustrating the Run Physical Exam process of FIG. 5.

FIG. 6 describes the run physical exam process 330 of FIG. 5 in more detail. Referring to FIG. 61, the process 330 begins at a start state 400 and moves to state 402 wherein the results of a neurological exam on the patient are received by the medical database system. A determination is then made at a decision state 404 whether the findings from the neurological exam are themselves a diagnosis. For example, a nonresponsive, flaccid neurological exam indicates a loss of consciousness diagnosis. If the findings are a diagnosis, the process 330 moves to a state 406 to record the diagnosis within the medical database system. If the finding is not a diagnosis, the process 330 moves to state 408 wherein the results of a skin exam are received by the medical database system.

Figure 6B:
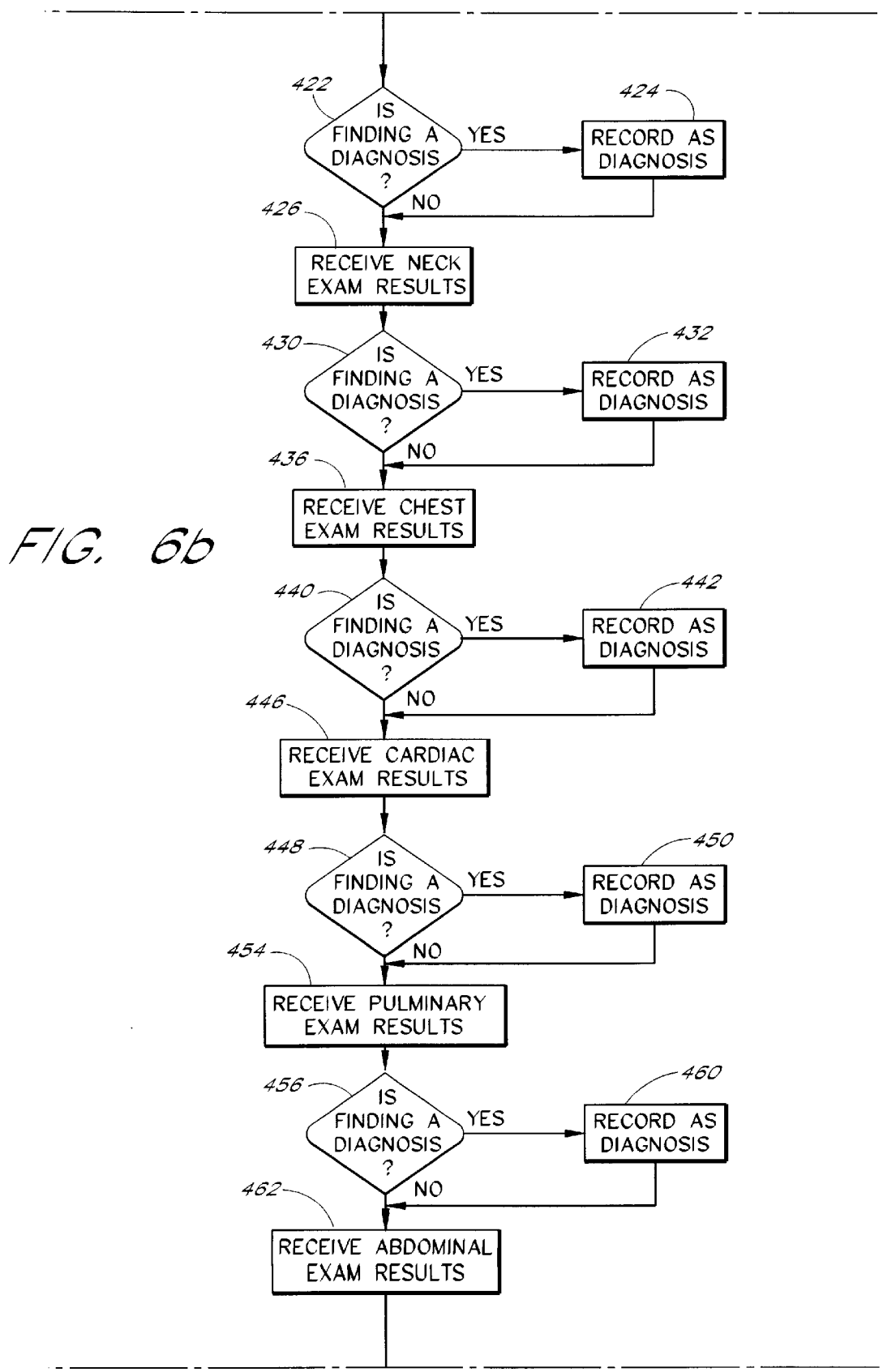

A determination is then made at a decision state 410 whether the results of the skin exam are a diagnosis. If the results are determined to be a diagnosis at the decision state 410, their diagnosis is recorded at a state 412 into the medical database system. If the results of the skin exam are not a diagnosis at the decision state 410, the process 330 moves to state 420 wherein the medical database system receives the results of a head, eyes, ears, nose and throat exam. Now referring to FIG. 6*b*, the process 330 then moves to a state 422 to determine whether the results from this exam are a diagnosis. If the results are a diagnosis, they are recorded at a state 424 and the process moves to a state 426 wherein the results of a neck exam are received. If a finding were not a diagnosis at the decision state 422, the process 330 moves directly to the state 426.

Once the results of a neck exam are received at the state 426, a determination is made at the decision state 430 whether the results of the neck exam are a diagnosis. If the findings are a diagnosis, the process 330 moves to state 432 wherein the diagnosis is recorded into the medical database system. If the finding is not a diagnosis, the process 330 moves to a state 436 wherein the results of a chest exam are received into the medical database system. The process 330 then moves to a decision state 440 wherein a determination is made whether the results of the chest exam are a diagnosis. If the results of the chest exam are a diagnosis, the process 330 moves to state 442 and records the diagnosis in the medical database system.

The process 330 then moves to a state 446 and receives the results from a cardiac exam from the patient. A determination is then made at a decision state 448 whether the results of the cardiac exam are a diagnosis. If the results are a diagnosis, the process 330 moves to a state 450 and records the results of the cardiac exam as a diagnosis in the medical database system. The process 330 then moves to a state 454 wherein the results of a pulmonary exam are received in the medical database system. A determination is then made at a decision state 456 whether the findings from the pulmonary exam are a diagnosis. If the findings are a diagnosis, the process 330 moves to a state 460 wherein the diagnosis is recorded in the medical database system.

Figure 6C:
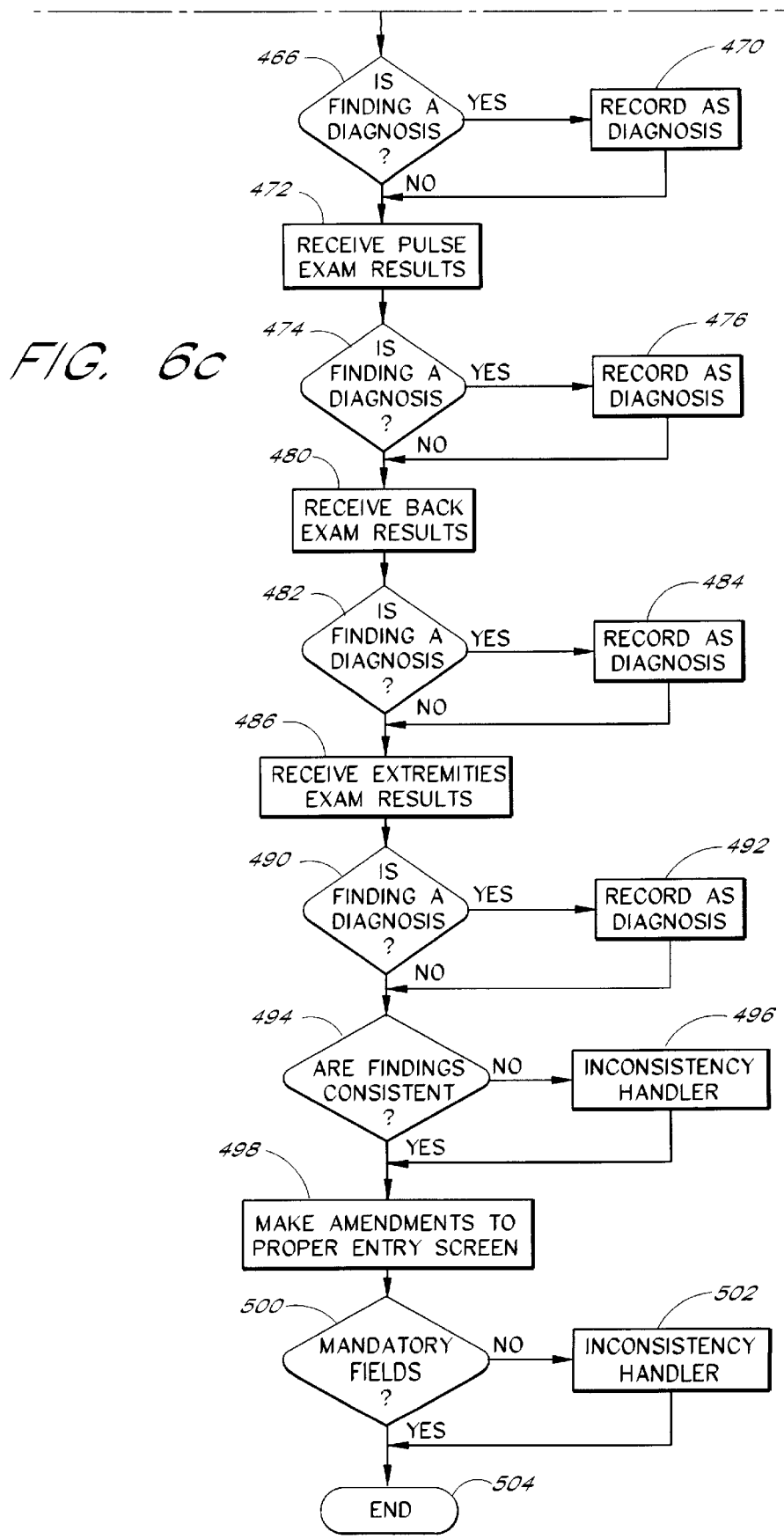

The process 330 then moves to a state 462 wherein the results of an abdominal exam on the patient are received by the medical database system. Now referring to FIG. 6c, the process 330 then moves to a state 466 wherein a determination is made whether the findings from the abdominal exam are a diagnosis. If the findings are a diagnosis, the process 330 records these findings at a state 470 and moves to a state 472 wherein the results of a pulse exam are received into the medical database system. As is known, a pulse exam typically includes interval recordings or blood pressure, heart rate, respiratory rate and pulse oximetry.

Once the results of the pulse exam are received at the state 472, a determination is made at a state 474 whether the findings from the pulse exam are a diagnosis. If the findings are a diagnosis, they are recorded at a state 476 and the process thereafter moves to a state 480 wherein the results of a back exam are received. If the findings from the pulse exam are not a diagnosis, the process 330 moves directly from the decision state 474 to the state 480.

Once the results of the back exam are received at the state 480, the process 330 moves to a decision state 482 wherein a determination is made whether the findings from the back exam are a diagnosis. If the findings are a diagnosis, the process 330 records the diagnosis at a state 484 and moves to a state 486 wherein the results of an extremities exam are received by the medical database system.

If a determination were made that the finding was not a diagnosis at the decision state 482, the process 330 moves directly to the state 486. One the results of the extremities exam are received by the medical database system, the process 330 moves to a state 490 wherein a determination is made whether the findings from the extremities exam are a diagnosis. If the findings are a diagnosis, they are recorded in a state 492 and the process 330 thereafter moves to a decision state 494 to determine whether the findings throughout the process 330 are consistent with one another and the trauma scores. For example, a normal verbal response would not be consistent with a flaccid neurological finding. Similarly, a normal respiratory score may not be consistent with a tension pheumothorax finding.

If the findings are inconsistent, the process 330 moves to an inconsistency handler 496 to request information from the emergency medical team why the findings are inconsistent with one another. Once the inconsistency handler 496 has determined that the findings are now consistent, the process 330 moves to a state 498 wherein any amendments are made to the proper physical exam record. The process 330 then moves to a decision state 500 wherein a determination is made whether all of the mandatory fields have been completed for this module. If the mandatory fields have not been completed, the process 330 moves to an error handler 502 to request information about the empty, mandatory fields. The process 330 then terminates at an end state 504.

B) The Process of Determining a Diagnosis and Rank

FIG. 7 describes the process 360 of determining the diagnosis and rank for a patient (FIG. 5) in more detail. The process 360 begins at a start state 550 and then moves to a state 552 wherein a list of possible diagnoses is generated based on the results of the clinical exam. Thus, the suggested diagnoses are linked to the physical exam scores received earlier by the system. The patient historical data, physical exam data and procedural data are all taken into account when the system calculates possible diagnoses.

For example, if an unconscious patient with a head injury documented in history and the physical exam might be linked to a "acute closed head injury with loss of consciousness" diagnosis. However, if a member of the emergency medical team had inadvertently chosen in the chart that the patient was verbalizing normally, the system would request an explanation of the discrepancy.

Once the list of possible diagnoses are presented at state 552, the process 360 then moves to a decision state 556 to determine whether any diagnoses from the generated list are consistent with the results of the clinical exam. If a determination is made that none of the diagnoses are consistent with the results from the clinical exam, the process 360 moves to a state 558 wherein a diagnosis is requested from the emergency medical team. The process 360 then moves to a decision state 560 wherein the diagnosis entered by the emergency medical team is correlated with the results from the clinical exam. If the results do not correlate, the process 360 moves to a state 564 wherein the medical database system requests an explanation of the discrepancy between the entered diagnoses and results of the clinical exam. The explanation and diagnoses are then recorded in the medical database system at a state 566. The process 360 then moves to a state 570 wherein a diagnosis is selected.

However, if any diagnosis were determined to be consistent at the decision state 556, or if any input diagnosis correlated with the results of the clinical exam, the process 360 would move immediately to the state 570 wherein one of the diagnoses is selected. The process 360 then moves to a state 574 wherein a treatment protocol is suggested based on the diagnosis selected at the state 570. For example, an intubation protocol might be suggested based on a heart attack diagnosis. The process 360 then moves to a state 576 wherein the ICD-9 code is retrieved for the suggested treatment protocol from state 574. A determination is then made at a state 578 whether the ICD-9 code is complete, including all subcode numbers. If the code is incomplete, the process 360 displays a list of potential subcodes at a state 580 and the process moves to a state 582 wherein the proper code is selected from the list. The process 360 then returns to state 576 to retrieve the proper ICD-9 code. If a determination was made at the decision state 578 that the complete ICD-9 code was retrieved, the process terminates at an end state 590.

3) The Administration Module

Figure 8:
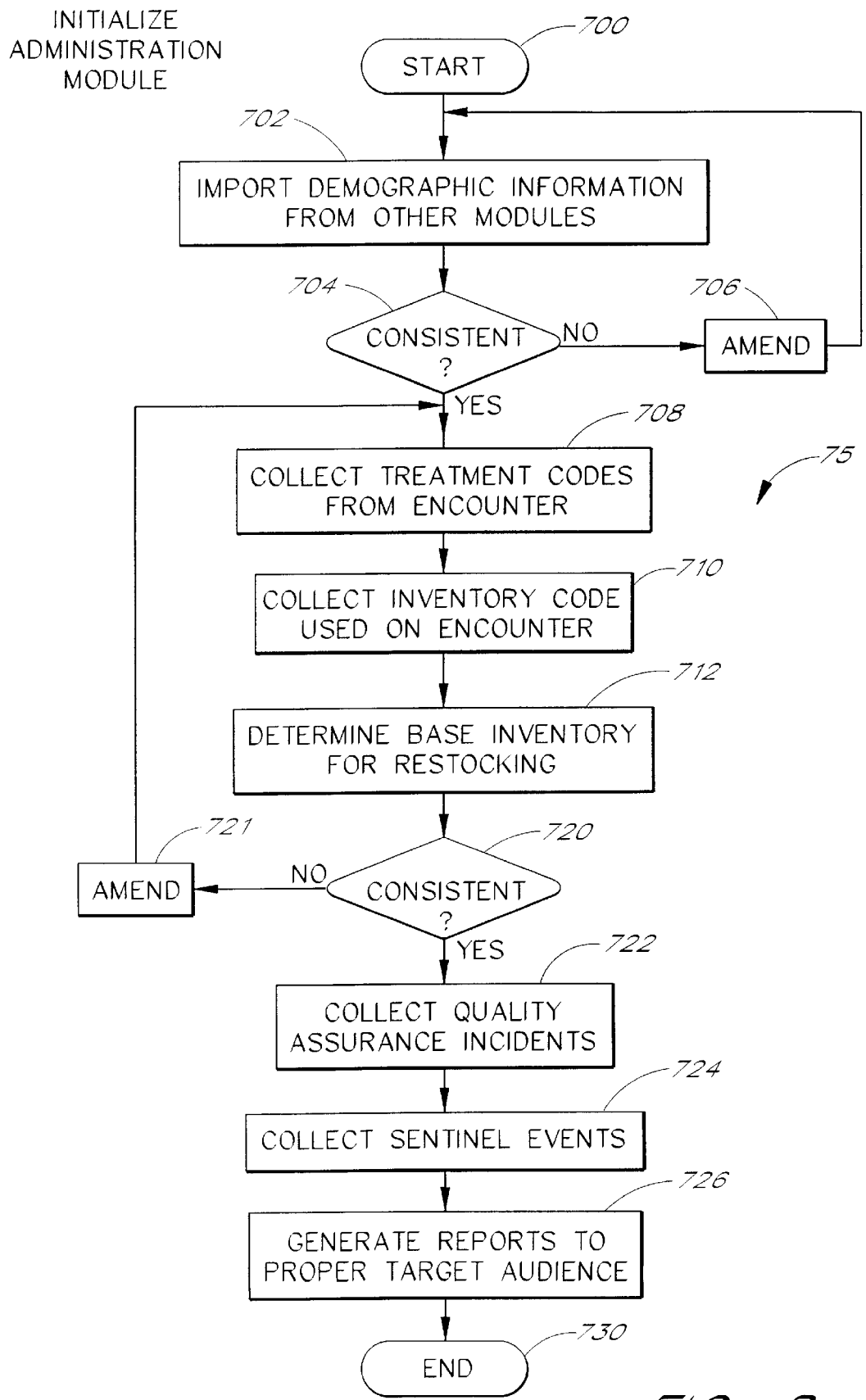
FIG. 8 is a flow diagram illustrating the Initialize Administration Module process of FIG. 2.

Referring now to FIG. 8, the initialize administration module process 75 (FIG. 2) is described in more detail. The process 75 begins at a start state 700 and then moves to state 702 wherein the demographic information from the other software modules within the medical database system are imported into the administration module. The process then moves to a decision state 704 wherein a determination is made as to whether the demographic information is consistent with the information contained in the other modules. For example, a patient's name might be recorded differently in the dispatch and clinical modules. Similarly, the social security number or insurance information might be inconsistent between modules. If the information is inconsistent, the process 75 moves to a state 706 wherein the information is amended to conform with the data within the other modules. The process then returns to the state 702 to re-import the demographic information.

If a determination were made at the decision state 704 that the demographic information was consistent between each module, the process 75 moves to a state 708 wherein the treatment codes from the patient encounter are collected into the medical database system. The process then moves to a state 710 wherein the inventory codes, such as ICD-9, are collected into the administration module of the medical database system. The process 75 then moves to a state 712 wherein a calculation is performed to determine the amount of inventory needed to restock the base station so that an ample quantity of medical supplies will also be available to the emergency medical team. The process 75 then moves to a decision state 720 to determine whether the treatment codes, inventory codes and base inventory calculations are consistent with one another. For instance, was an intubation tube used for a warranted intubation and not for a pericaridocentesis procedure. Further, this decision checks that the amount and coding of the used supplies are correct and that, for example, an intubation tube is recorded and not a chest tube. If a determination is made that the data are not consistent, the process 75 makes amendments at a state 721 and returns to the state 708. If a determination is made that the data are consistent, the process 75 moves to a state 722 wherein the quality assurance incidents are collected. The quality assurance incidents can include procedure complications, equipment difficulties, crew interaction problems and organizational mismanagement.

The process 75 then moves to a state 724 wherein any sentinel events that occurred during the patient encounter are collected into the administration module. As discussed previously, a sentinel event is one which might require notification to a third party. Such an event might be repeated failed procedures by a crew member, prolonged scene times, incorrect administration of medicine, performance of non-indicated procedures and unwarranted deviation from treatment protocols. The process 75 then moves to a state 726 wherein reports are generated from the administration module to the proper target audience. The target audiences may include administrators, collectors, insurers, supervisors, medical directors and governmental organizations. The process 75 then terminates at an end state 730.

A) The Collecting a Treatment Plan Process

Figure 9B:
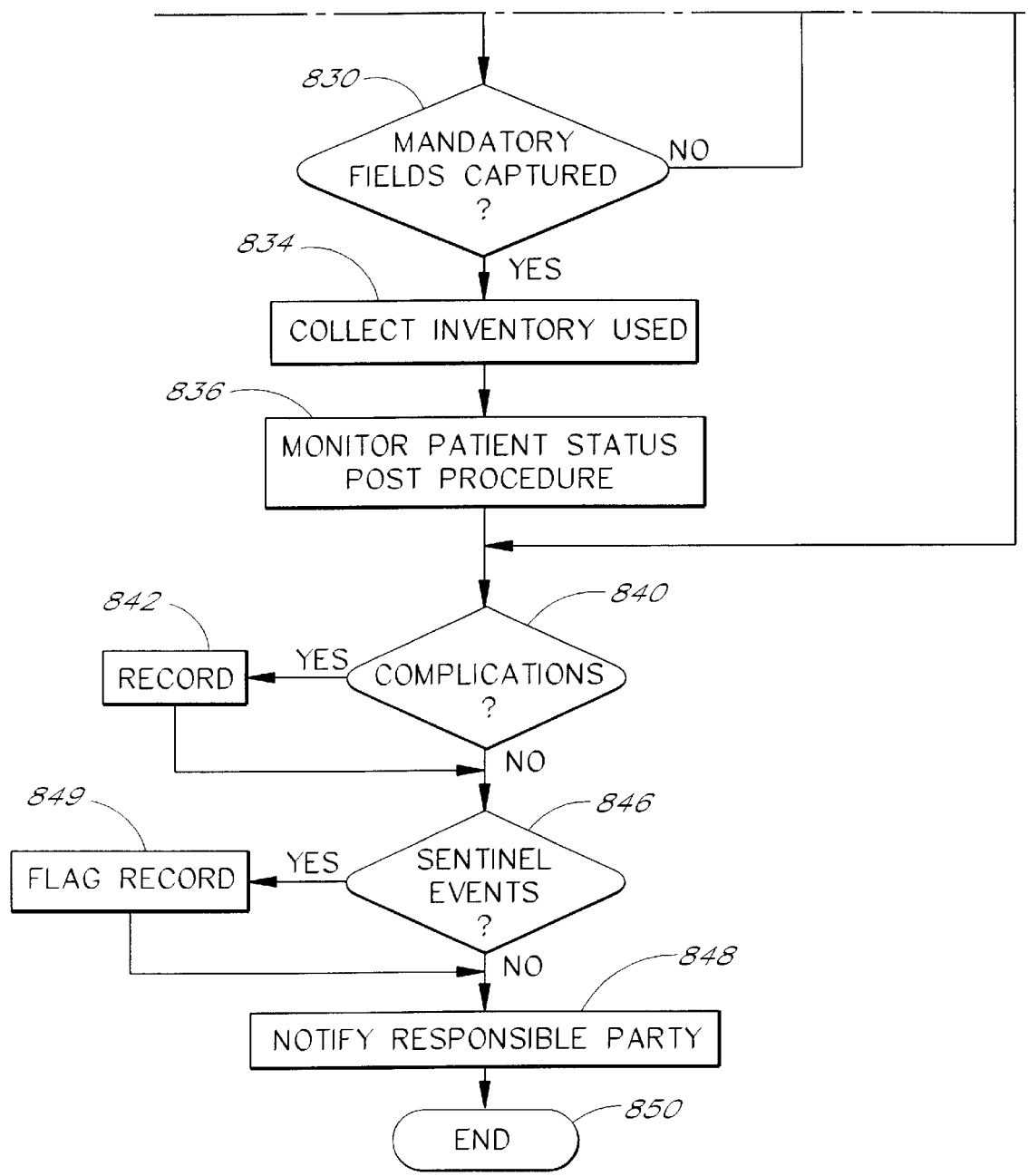
FIG. 9 is a flow diagram illustrating the Advanced Procedure Treatment process of FIG. 5.

Referring now to FIG. 9a, the process of collecting a treatment plan 370 (FIG. 5) is described in more detail. The process 370 begins at a start state 800 and moves to a state 802 wherein the patient's Basic Life Support (BLS) treatment information is collected by the medical database system. The BLS treatment information might include vital signs, results of an initial survey, fluid balances and immobilization procedures.

The process 370 then moves to a state 804 wherein the patient status is monitored by the emergency medical team. The status is then updated into the medical database system as changes occur in the patient's condition. The process 370 then moves to a decision state 810 wherein a determination is made whether any advanced procedures were administered to the patient. If advanced procedures were administered to the patient, the process 370 moves to a state 812 wherein the indications for the patient are recorded within the medical database system. A determination is then made at a state 814 whether the recorded indications are consistent with the results of the clinical exams and the vital signs. This feature of the system provides an efficient correcting mechanism and ensures that accurate information is entered into the system.

If a determination is made at the decision state 814 that the indications are consistent, the process 370 moves to a state 820 wherein the procedures used on the patient are recorded. However, if a determination is made at the decision state 814 that the findings and vital signs are not consistent with the recorded indications, the process 370 moves to a state 822 wherein the indications, findings or vital signs, can be amended within the medical database system. The process 370 then returns to the state 820.

Once the procedures are recorded at the state 820, the process 370 moves to a state 822 wherein any procedure notes can be entered into the medical database system. The process then moves to a decision state 830 (FIG. 9b) wherein a determination is made whether all of the mandatory fields have been captured in the treatment record. If some of the mandatory fields have not been captured, the process 370 returns to state 820 wherein the attending emergency medical personnel are prompted to enter data into the mandatory fields. However, if a determination is made that the mandatory fields have been captured, the process moves to a state 834 wherein the inventory used in the advanced procedures are collected. Because the inventory used is collected at the incident scene, it is less likely that some inventory will be forgotten to be entered. In addition, validity checking can be done to ensure that the inventory used correlates with the treatments that were performed.

The process then moves to a state 836 wherein the patient status following the procedure is monitored and any indications are input into the medical database system. The process 370 then moves to a decision state 840 wherein a determination is made whether any complications exist such as esophageal intubation, broken teeth or excessive bleeding that should be recorded into the medical database system. If such complications do exist, the process moves to a state 842 and records the complications in the medical database system log. The process 370 then moves to a decision state 846 wherein a determination is made whether any sentinel events occurred during the treatment.

If no sentinel events did occur, the process moves to a state 848 wherein the party responsible for the patient, such as the hospital, is notified. However, if any sentinel events did occur, the process 846 moves to a decision state 849 wherein the record for that patient is flagged to indicate that sentinel events occurred during the treatment period. The process then returns to the state 848 and terminates at an end state 850.

4) The Billing System

Figure 10B:
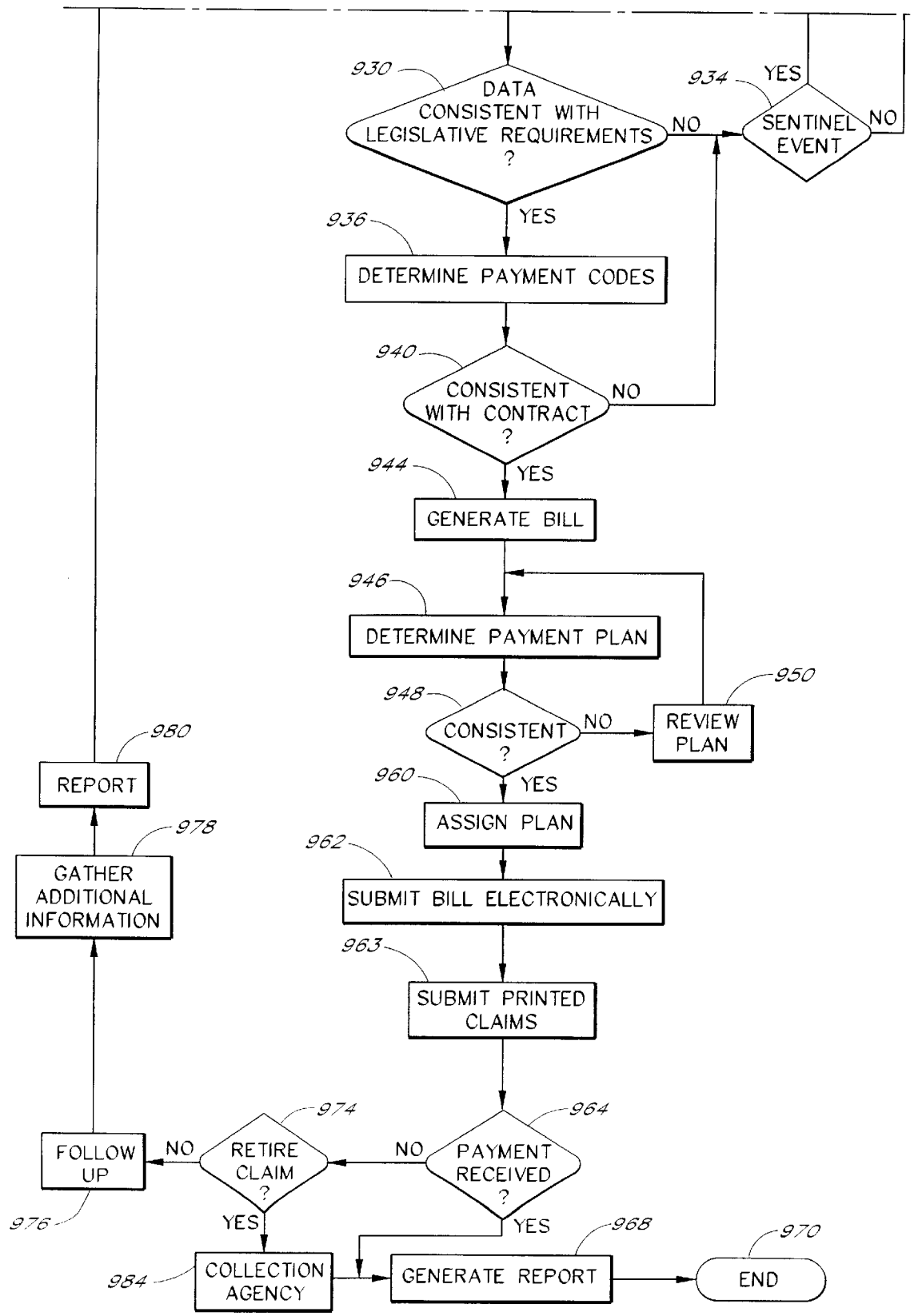
FIG. 10 is a flow diagram illustrating the Initialize Billing Module process of FIG. 2.

Referring now to FIG. 10, the initialize billing module process 80 (FIG. 2) is described in more detail. The process 80 begins at a start state 900 and then moves to a state 902 wherein a unique invoice number is generated for the bill. The process 80 then moves to a state 904 wherein a particular person (e.g.; a collector) is assigned to the invoice number generated at the state 902. The collector is responsible for tracking the progress of the invoice to ensure that it is eventually paid. Once a collector has been assigned at the state 904, the process 80 moves to a state 906 wherein the payor/demographic data is collected to identify the insurance company, HMO or individual patient responsible for paying the outstanding bill. The process 80 then moves to a state 908 wherein the clinical diagnosis data from the patient encounter is collected into the billing module. This information is used to describe the clinical encounter on the bill.

The process 80 then moves to a state 910 wherein the clinical procedure data from the clinical encounter is collected into the billing module. The clinical procedure data includes all of the procedures performed by the emergency medical team at the incident site. The specific treatments given to the patient at the incident site are then collected into the billing module at a state 912. The process 80 then moves to a state 920 wherein the inventory data corresponding to the number of syringes, drugs and other paraphernalia used by the emergency medical team are collected.

Once all of the data from the states 906 to 920 are collected, a determination is made at a decision state 924 whether there is any new data to be entered into the system. New data could relate to updated insurance policy information, patient addresses or any other data that needs to be amended or added. If a determination is made that new data does exist, the process 80 moves to a state 926 wherein the appropriate data is amended so that it can be extracted.

If a determination is made at the decision state 924 that there is no new data to enter, the process 80 moves to a decision state 926 to determine whether the extracted data is consistent with the requirements of the payor. For example, the payor may require that the inventory data include the name of the address of the vendor responsible for selling the medical equipment inventory item. If this information was not collected with the inventory data, it would be inconsistent with the payor requirements. If a determination is made that the data is inconsistent with the payor requirements, the process 80 returns to state 926 so that the data can be amended.

However, if the data is consistent with the payor requirements at the decision state 926, the process 80 moves to a decision state 930 to determine whether the data is consistent with legislative and regulatory requirements. The legislative requirements may relate, for example, to the specific dosages and types of drugs given to the patient during the encounter. Other legislative requirements may relate to the personnel configurations required for patient transport, procedure practices or types of necessary documentation. For example, it may be required that at least one doctor, one nurse and one emergency medical technician be sent to every call. If the data is inconsistent with legal requirements, the process 80 moves to a decision state 934 to determine whether the data relates to a sentinel event that occurred during the patient encounter. If a sentinel event did not occur, the process 80 returns to the state 926 so that the data can be amended to indicate the nature of the inconsistency. However, if the data did relate to a sentinel event, the process 80 moves to a state 936 to flag the data as a sentinel event (as defined above). This flag can then alert the payor that a sentinel event occurred which may require a special billing procedure.

If a determination is made that the data was consistent with legislative requirements at the decision state 930, the process 80 moves to a state 934 wherein the payment codes corresponding to all of the data is determined. The payment codes can be the industry standard ICD-9 codes or any other code required by the payor.

The process 80 then moves to a decision state 940 to determine whether the payment codes are consistent with the payor's contract. Normally, each payor's requirements are programmed into the billing module. These requirements usually relate to the format and content of the invoice. If a determination is made that the payment codes and data are inconsistent with the contract, the process moves to the decision state 934 to determine whether a sentinel event had occurred. As discussed above, sentinel events can be events that happen during the patient encounter that are worthy of special attention. The occurrence of a sentinel event might be one reason the payment codes are inconsistent with the contract terms at the decision state 940. For example, a misdiagnosis leading to an improper treatment would be one type of sentinel event that could lead to a treatment code not corresponding properly with a diagnosis code in the contract.

If the payment codes and data were consistent with a contract, the process 80 generates a bill at a state 944 and moves to a state 946 to determine the proper payment plan for this payer. For example, the payment plan might be a net payment due in 60 days with a 2% discount for payments made within 30 days. A determination is then made at a decision state 948 whether the payment plan chosen is consistent with the requirements from the patient's health care providing entity or institution. If a determination is made that the payment plan is not consistent, the process 80 moves to a state 950 wherein the payment plan is reviewed. The process 80 then returns to state 946 to determine a new payment plan.

If a determination is made at the decision state 948 that the payment plan is consistent with the contract, the plan is assigned at a state 960 and an electronic bill is submitted via, for example, an electronic communication or computer diskette at a state 962. A printed copy of the claims can then be submitted to the appropriate insurance company or agency at a state 963. The process then moves to a decision state 964 to determine if any payment has been received. If a determination is made at the decision state 964 that payment has been received for the bill submitted at the state 962, a report is generated at a state 968 and the process terminates at an end state 970.

However, if a determination is made that the payment has not been received at the decision state 964, the process 80 makes a decision whether to retire the insurance claim of a specific amount of money at a decision state 974. As is known in the art, to retire a claim is to flag it as uncollectable so that a collection agency is thereafter involved. If a determination is made at the decision state 974 that the claim is not to be retired, the process 80 moves to a state 976 wherein a follow-up on the bill is performed to gather more information concerning the payment. For example the number of days can be calculated between the invoice date and the current date to determine if the payment is late. The process 80 then gathers additional information from the payer at a state 978 and generates a billing report listing the accounts receivable at a state 980. The process then returns to the state 924 to determine whether all data had been extracted from the other modules.

If a determination is made at the decision state 974 to retire the claim, a collection agency is notified at a state 984 and the process thereafter moves to the state 968 to generate reports concerning the outstanding bill.

While the invention has been described in connection with specific embodiments thereof, it will be understood that it is capable of further modification, and this application is intended to cover any variations, uses, or adaptations of the invention following, in general, the principles of the invention and including such departures from the present invention as would be understood to those in the art as equivalent and the scope and context of the present invention is to be interpreted as including such equivalents and construed in accordance with the claims appended hereto.

What is claimed is:

1. A computerized integrated data management system for tracking a patient incident, comprising:

a first module capable of dispatching an emergency transport crew specific to a patient incident requiring emergency medical care by the emergency transport crew, wherein transportation tracking information relating to the dispatch is recorded; and a second module capable of receiving information from the first module and billing the patient appropriately for costs indicative of the patient incident, including transportation costs.

2. The data management system of claim 1, further comprising a third module capable of interpreting data relating to the medical condition of a patient involved in the patient incident and determining a diagnosis for the patient.

3. The data management system of claim 2, wherein the third module includes instructions for displaying a plurality of diagnoses.

4. The data management system of claim 2, wherein the third module includes a communication interface for automatically reading a patient's vital signs.

5. The data management system of claim 2, wherein the second module includes instructions for marking selected information as sentinel events.

6. The data management system of claim 1, wherein the first module includes instructions for dispatching a helicopter.

7. The data management system of claim 6, wherein the first module includes instructions for tracking the flight path of the helicopter.

8. The data management system of claim 1, wherein the first and second modules communicate via a shared database.

9. The data management system of claim 1, wherein the first and second modules are executed on a portable computer.

10. A computerized integrated data management system for tracking a patient incident, comprising:

a first module capable of interpreting data relating to the medical condition of a patient involved in a patient incident requiring emergency medical care by an emergency medical transport crew and determining a diagnosis for the patient, wherein the first module prompts for physical findings relating to a physical examination of the patient at the site of the patient incident; and a second module capable of receiving information from the first module and billing the patient appropriately for the patient incident.

11. The data management system of claim 10, wherein the first and second modules are executed on a portable computer.

12. The data management system of claim 10, wherein the first module includes instructions for displaying a plurality of diagnoses.

13. The data management system of claim 10, wherein the first module includes a communication interface for automatically reading a patient's vital signs.

14. The data management system of claim 10, wherein the first module includes instructions for marking selected information as sentinel events.

15. A computerized method of generating a patient encounter record, comprising the steps of:

collecting flight information relating to an emergency transport crew dispatch;

collecting patient information from a clinical encounter associated with a patient incident requiring emergency medical care by the emergency transport crew; and integrating the patient information with the flight information to produce an encounter record indicative of the patient's clinical encounter.

16. The computerized method of claim 15, wherein the method is performed a plurality of times to generate a plurality of patient encounter records.

17. The computerized method of claim 16, further comprising the steps of:

extracting data from the plurality of patient encounter records; and generating statistical information relating to the clinical encounter to justify the cost of dispatching the emergency transport crew.

18. The computerized method of claim 15, wherein the step of collecting flight information includes collecting flight information for a helicopter dispatch.

19. The computerized method of claim 15, wherein the step of collecting patient information includes automatically collecting patient information from emergency medical equipment.

20. The computerized method of claim 15, wherein the step of collecting patient information includes the step of determining whether a sentinel event has occurred.

21. The computerized method of claim 20, wherein the step of collecting patient information includes the step of marking sentinel events with a flag.

22. The computerized method of claim 15, wherein the step of integrating the patient information includes the step of determining whether the flight information and patient information are internally consistent.

23. A method of diagnosing an illness in a patient, comprising the computer implemented steps of:

collecting information from a physical exam at the site of a patient's incident requiring emergency medical care by an emergency medical transport crew;

determining a list of possible diagnoses based on the physical exam; and recording the diagnosis results in a centralized database of patient emergency medical information; and recording a treatment of the patient at the site of the patient incident.

24. The method of claim 23, wherein the collecting step includes automatically collecting physical exam information from emergency medical equipment.

25. The method of claim 23, wherein the determining step includes displaying the diagnosis on the display of a computer.

26. The method of claim 23, wherein the steps form a computer program stored in a memory.

27. The method of claim 26, wherein the memory is selected from the group consisting of: RAM, ROM, a hard disk and a floppy disk.

* * * * *

(12) EX PARTE REEXAMINATION CERTIFICATE (7687th)
United States Patent
Jones et al.

(10) Number: US 6,117,073 C1
(45) Certificate Issued: Aug. 17, 2010

(54) INTEGRATED EMERGENCY MEDICAL TRANSPORTATION DATABASE SYSTEM

(75) Inventors: Scott J. Jones, Carlsbad, CA (US); Kevin C. Hutton, San Diego, CA (US)

(73) Assignee: Golden Hour Data Systems, Inc., Solana Beach, CA (US)

Reexamination Request:
No. 90/010,531, May 7, 2009

Reexamination Certificate for:
Patent No.: 6,117,073
Issued: Sep. 12, 2000
Appl. No.: 09/033,440
Filed: Mar. 2, 1998

(51) Int. Cl.
*A61B 5/00* (2006.01)

(52) U.S. Cl. .................................. 600/300; 705/2; 705/3
(58) Field of Classification Search .................. None
See application file for complete search history.

(56) References Cited

U.S. PATENT DOCUMENTS

| | | |
|---|---|---|
| 1,873,126 A | 8/1932 | Hugershoff |
| 2,977,177 A | 3/1961 | McLaughlin et al. |
| 3,921,318 A | 11/1975 | Calavetta |
| 4,221,404 A | 9/1980 | Shuffstall |
| 4,236,332 A | 12/1980 | Domo |
| 4,814,711 A | 3/1989 | Olsen et al. |
| 4,819,053 A | 4/1989 | Halavais |
| 4,858,121 A | 8/1989 | Barber et al. |
| 5,122,959 A | 6/1992 | Nathanson et al. |
| 5,146,439 A | 9/1992 | Jachmann et al. |
| 5,283,829 A | 2/1994 | Anderson |
| 5,327,341 A | 7/1994 | Whalen et al. |
| 5,465,206 A | 11/1995 | Hilt et al. |
| 5,483,443 A | 1/1996 | Milstein et al. |
| 5,508,912 A | 4/1996 | Schneiderman |
| 5,544,044 A | 8/1996 | Leatherman |
| 5,550,976 A | 8/1996 | Henderson et al. |
| 5,619,991 A | 4/1997 | Sloane |
| 5,734,706 A | 3/1998 | Windsor et al. |
| 5,761,278 A | 6/1998 | Pickett et al. |
| 5,805,670 A | 9/1998 | Pons et al. |
| 5,867,821 A | 2/1999 | Ballantyne et al. |
| 5,874,897 A | 2/1999 | Klempau et al. |
| 5,900,883 A | 5/1999 | Crucs |
| 5,911,132 A | 6/1999 | Sloane |
| 5,940,013 A | 8/1999 | Vladimir et al. |
| 5,974,355 A | 10/1999 | Matsumoto et al. |
| 6,029,144 A | 2/2000 | Barrett et al. |
| 6,044,323 A | 3/2000 | Yee et al. |
| 6,106,459 A | 8/2000 | Clawson |
| 6,151,581 A | 11/2000 | Kraftson et al. |
| 6,324,516 B1 | 11/2001 | Shults et al. |
| 6,438,533 B1 | 8/2002 | Spackman et al. |
| 6,529,876 B1 | 3/2003 | Dart et al. |
| 6,725,209 B1 | 4/2004 | Iliff |
| 6,751,630 B1 | 6/2004 | Franks et al. |
| 6,785,410 B2 | 8/2004 | Vining et al. |
| 6,868,074 B1 | 3/2005 | Hanson |

(Continued)

FOREIGN PATENT DOCUMENTS

| | | |
|---|---|---|
| EP | 1990748 A1 | 11/2008 |
| JP | 01319861 A | 12/1989 |
| WO | WO03102726 | 12/2003 |

OTHER PUBLICATIONS

AeroMed Software, *Flight Management Module Version 2.2 Reference Manual* (rev. Nov. 10, 1992, copyright 1993).

(Continued)

*Primary Examiner*—Joseph A. Kaufman

(57) ABSTRACT

An integrated medical database system for the emergency medical transportation business is disclosed. The system includes a dispatch module, clinical module, administration module and billing module. Each module may communicate data with one or more of the other modules to form a system incorporating data sharing, thus achieving an end-to-end automation of emergency medical care accounting. Internal consistency checks are performed by the system to ensure that proper treatments are performed according to a chosen diagnosis.

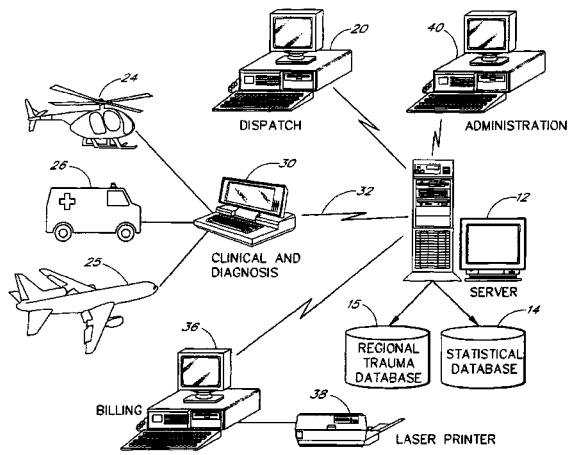

U.S. PATENT DOCUMENTS

| | | |
|---|---|---|
| 6,915,265 B1 | 7/2005 | Johnson |
| 7,233,905 B1 | 6/2007 | Hutton et al. |
| 2001/0034618 A1 | 10/2001 | Kessler et al. |
| 2002/0004729 A1 | 1/2002 | Zak et al. |
| 2002/0010679 A1 | 1/2002 | Felsher |
| 2002/0120846 A1 | 8/2002 | Stewart et al. |
| 2003/0036683 A1 | 2/2003 | Kehr et al. |
| 2003/0093320 A1 | 5/2003 | Sullivan |
| 2005/0240613 A1 | 10/2005 | Logan |
| 2007/0203742 A1 | 8/2007 | Scott et al. |
| 2008/0126134 A1 | 5/2008 | Jones et al. |

OTHER PUBLICATIONS

*Transmonde Introduces New Notebook Configurations,* PC Business Products, Feb. 1997.
Gai Elhanan, M.D., Socrates A. Socratous, James J. Cimino, M.D., *Integrating DXplain into a Clinical Information System using the World Wide Web,* In Cimino JJ, ed.Proceedings of the American Medical Informatics Association Annual Fall Symposium (formerly SCAMC); Washington, DC; October, Hanley & Belfus, Philadelphia, 1996:348–352.
Public Law 104–191, Health Insruance Portability and Accountability Act of 1996, published Aug. 21, 1996.
Wyoming Medicaid Provider Manual Billing Manuals, Mar. 1, 1999, Section on HCFA 1500, chapters 4 (pp. 4–4, 4–7 and 4–54 in particular) and 9 (pp. –11 and 9–13). Section on Transportation, chapter 3 (3–12 to 3–22 in particular) and Appendices (C, D) 104 pages.
Schriewer, "Airborne Ambulance Saves Precious Time," Tulsa World, May 22, 1996, pp. 1–2.
Hudson, "Attorneys Fear Patient Transfer Claims in Malpractice Cases," Hospitals, Apr. 5, 1991, vol. 65, issue 7, pp. 44–48.
Segroves, "Navigation systems aids medical flights Bad weather landings are now possible at hospitals," News Sentinel, Aug. 7, 1994, pp. D7–8.
Spencer, Thomas, "Contracting for helicopter emergency transport services," Healthcare Financial Management, Aug. 1993, pp. 67–72.
Report on EMS Software Providers, "Interfacing Modules; The Industry Standard," dated Jul. 2007.
SweetTalk newsletter, dated Aug. 1993.
Various Sweet Computer Services, Inc.'s advertisements and brochures for SweetSoft™ software.
Rescue One, The Complete EMS Database Management Solution brochure.
Flightstar: A System Designed for Dispatchers, By Dispatchers flyer.
Computing Technologies for Aviation, Inc.'s Medical Air Transport System fact sheet, dated Sep. 1992.
Droege Computing Services Emergency Flight System handout.
EMS Consultants Ltd.—The Ultimate in EMS Software brochure.
EMS Expert @P–Docs flyer.
Westech System brochure.
LifeLink III reports.
Arec Data Management Systems Flyer.
Iris Product and Services handout.
DataWest's Air–Ops Version 2.1 software manual.
LiFlex Computer Aided Dispatch System flyer, dated 1991 or prior.
UCS Fire Rescue Incident Report, dated Mar. 7, 1994.
The Northern Virginia Sun article, dated May 10, 1993.
Weekly Business article, dated Feb. 14,1994.
UCS The EMS Commander brochure.
Fireline brochure.
UCS Pen Based Solutions for EMS brochure.
OuterLink web pages.
AeroMed Software Flight Management Module Version 2.2 Reference Manual, revised Nov. 10, 1992.
AeroMed Software Dispatch Module Version 2.2 Reference Manual, revised Nov. 10, 1992.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-27 is confirmed.

* * * * *